US008690325B1

(12) United States Patent
Straus et al.

(10) Patent No.: US 8,690,325 B1
(45) Date of Patent: Apr. 8, 2014

(54) SENSORY INPUT DEVICES, SENSORY OUTPUT DEVICES, AND AUTOMATIC SYSTEMS, METHODS, AND APPARATUSES FOR AT LEAST ONE OF MASS MEASUREMENT, EVALUATION, OR COMMUNICATION

(75) Inventors: Sandy Helene Straus, Tucson, AZ (US); Lawrence Straus, Boca Raton, FL (US)

(73) Assignees: Sandy Helene Straus, Tucson, AZ (US); Lawrence Straus, Boca Raton, FL (US)

( * ) Notice: Subject to any disclaimer, the term of this patent is extended or adjusted under 35 U.S.C. 154(b) by 0 days.

(21) Appl. No.: 13/068,758

(22) Filed: May 20, 2011

Related U.S. Application Data

(63) Continuation-in-part of application No. 11/333,953, filed on Jan. 17, 2006, now Pat. No. 8,016,416, and a continuation-in-part of application No. 11/484,614, filed on Jul. 12, 2006, now Pat. No. 8,323,025.

(60) Provisional application No. 60/697,950, filed on Jul. 12, 2005.

(51) Int. Cl.
*A61B 3/00* (2006.01)
*A61B 3/02* (2006.01)
*G02F 1/1335* (2006.01)

(52) U.S. Cl.
USPC ............................. 351/200; 351/222; 349/12

(58) Field of Classification Search
USPC ......... 351/200, 222–223, 237, 239, 240–244; 349/12, 16
See application file for complete search history.

(56) References Cited

U.S. PATENT DOCUMENTS

| 5,904,916 | A | 5/1999 | Hirsch |
|---|---|---|---|
| 5,956,125 | A | 9/1999 | Rosse et al. |
| 6,875,181 | B2 | 4/2005 | Kajimoto et al. |
| 7,165,973 | B2 | 1/2007 | Cantor |
| 8,016,416 | B1 | 9/2011 | Straus |
| 2006/0206833 | A1 | 9/2006 | Capper et al. |
| 2011/0107958 | A1 | 5/2011 | Pance et al. |
| 2012/0185942 | A1 * | 7/2012 | Dixon et al. ................... 726/24 |

\* cited by examiner

*Primary Examiner* — Dawayne A Pinkney

(57) ABSTRACT

Sensory input devices and sensory output devices for improving automatic systems, methods, and apparatuses are provided. In an embodiment, sensory input devices and sensory output devices are used to measure and evaluate at least one of cognition, knowledge, operation skills, physical properties, sensation, vision, or the like. In another embodiment, sensory input devices and sensory output devices are integrated to enhance communications. Such applications, among others, may include a plurality of sensors, actuator interfaces, or any combination thereof to optimize performance.

19 Claims, 15 Drawing Sheets

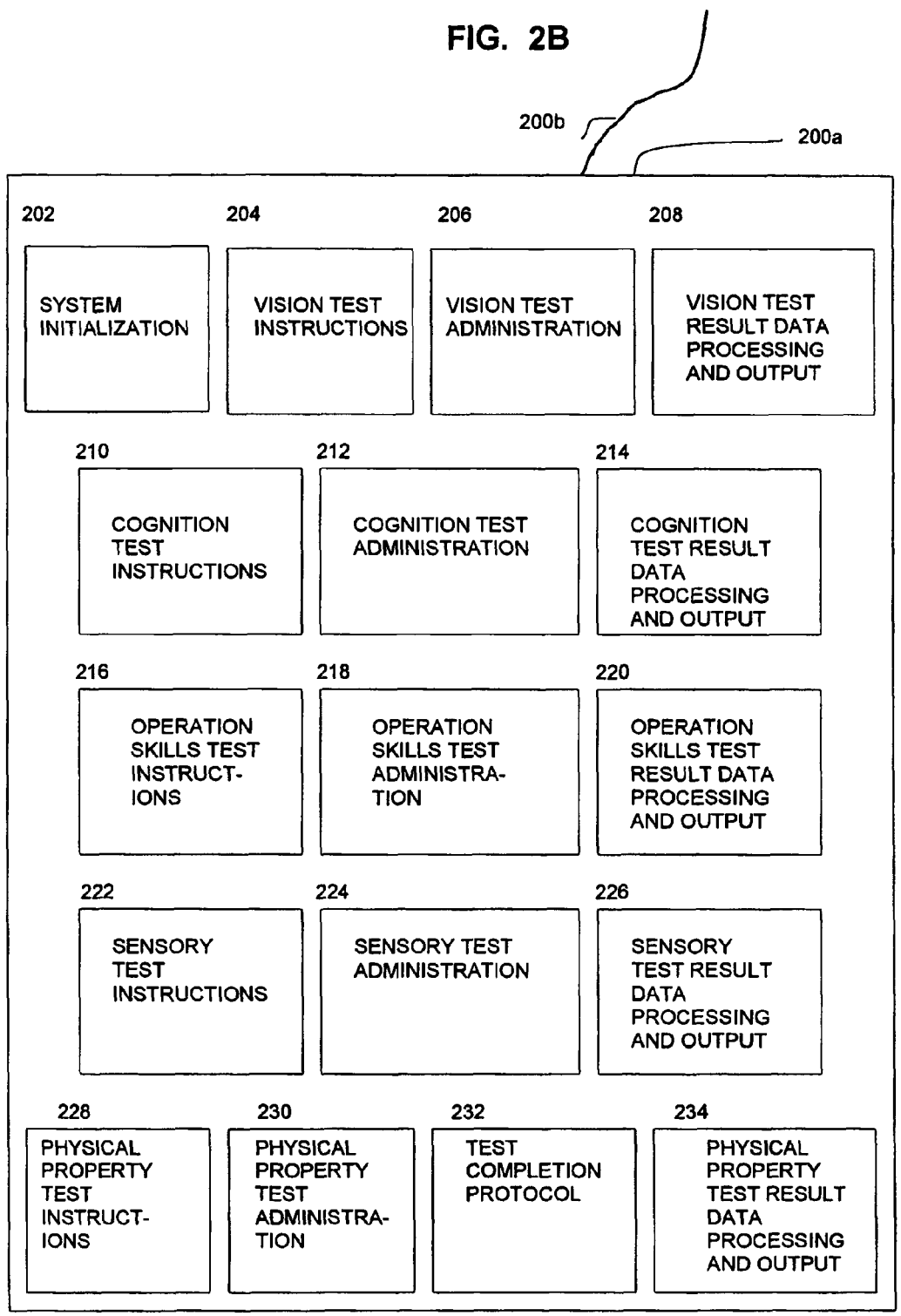

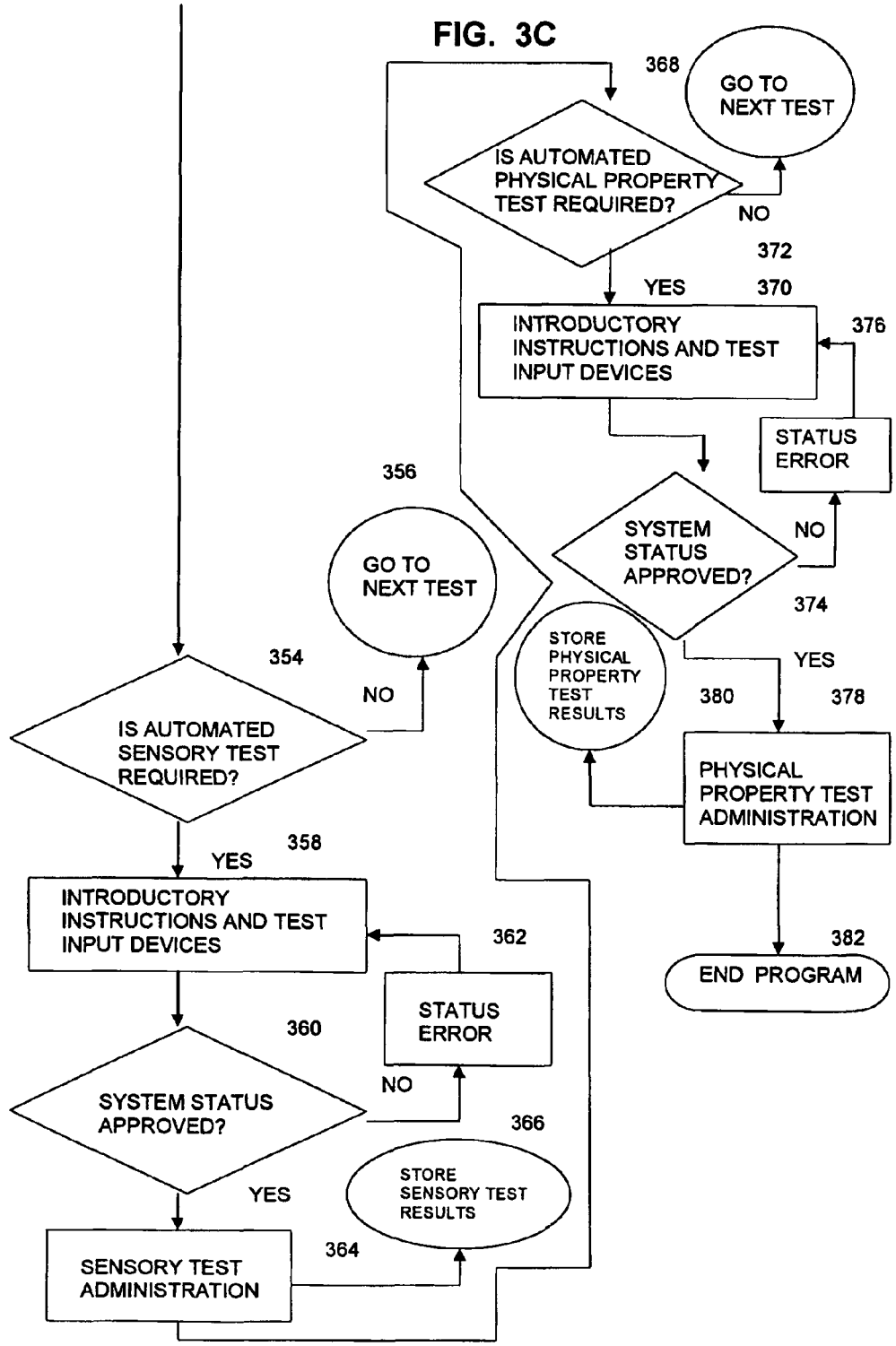

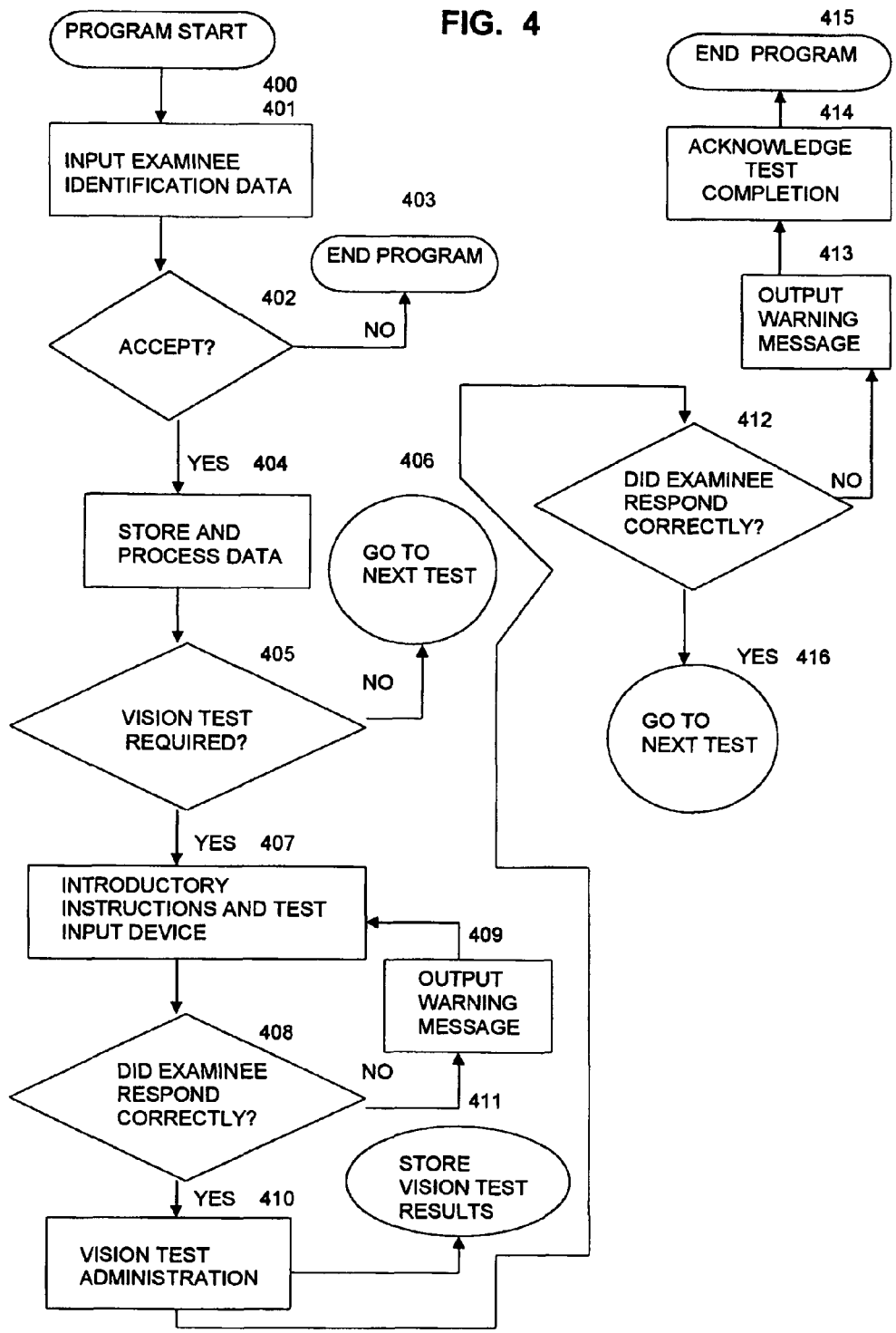

1000

1100

SENSORY INPUT DEVICES, SENSORY OUTPUT DEVICES, AND AUTOMATIC SYSTEMS, METHODS, AND APPARATUSES FOR AT LEAST ONE OF MASS MEASUREMENT, EVALUATION, OR COMMUNICATION

CROSS REFERENCE TO RELATED APPLICATIONS

This application is a continuation-in-part of application Ser. No. 11/333,953, filed Jan. 17, 2006, and is also a continuation-in-part of application Ser. No. 11/484,614 filed Jul. 12, 2006, which claims benefit to U.S. Provisional Patent Application No. 60/697,950, filed Jan. 12, 2005.

FEDERALLY SPONSORED RESEARCH

Not Applicable

SEQUENCE LISTING OR PROGRAM

Not Applicable

BACKGROUND

1. Field

This application relates to sensory input devices and sensory output devices and more particularly, but not exclusively, to such devices for use with automatic systems, methods, and apparatuses for measurement and evaluation of at least one of cognition, knowledge, operation skills, physical properties, sensation, vision, or the like.

2. Prior Art

Sensory input devices, sensory output devices, systems, and methods of their operation enhance the user experience through computing systems. Sensory input devices receive and process auditory, gustatory, kinesthetic, olfactory, tactile, vestibular, visual input from a user, sensory output devices provide auditory, gustatory, kinesthetic, olfactory, tactile, vestibular, visual stimulation to a user. Collectively, these devices, methods, and systems improve the use of automatic systems, methods, and apparatuses to measure and evaluate at least one of vision, cognition, knowledge, operation skills, physical properties, and sensation of the masses. Such enhanced measurements and evaluations engage those with lingual differences as well as incapacitated individuals, such as those with at least one of severe neuromuscular, visual, auditory, oral, or lingual conditions, among others, who preclude testing intraditional environments or certain automated settings.

Although automatic systems and methods are inexpensive to manufacture, the introduction, use, and application of sensory devices offer effective, rapid, uniform, simple, and eco-friendly testing and measuring of the masses. They also expand the pluralities and varieties of input and output device options that are now seriously limited. They also provide mechanisms for measurement and evaluation of physical properties and sensations—that are distinctively unique to each individual user.

U.S. Pat. No. 5,904,916 to Hirsch (1999) discloses a method of enhanced learning though administration of an inhalant. However, no automation devices, techniques, or methods are disclosed. In fact, paper and pencil cognitive tests, such as a trail making test, are cited for application. Furthermore, this enhanced learning instrument is limited to normosmic individuals and specific articles of manufacture.

U.S. Pat. No. 5,956,125 (1999) to Rosse et al. discloses a system and method for screening for dementia through the irradiation of an eye and the generation of signals. The system and methods are complex and clearly expensive to manufacture. They also do not appear to function autonomously.

U.S. Pat. No. 6,875,181 (2005) to Kajimoto et al. discloses a mentation test method and mentation test apparatus that is limited by functionality, display, and application. The method and apparatus do not appear to be useful for those with visual impairments.

U.S. Pat. No. 7,165,973 (2007) to Cantor discloses a method for non-verbal assessment of human competence that is limited to display, functionality, sequence, quantity, administration, classification categorization, and response. This method is clearly not capable of autonomous administration by paper or by computer.

U.S. 2006/0206833 A1 (2006) to Capper et al. discloses sensory output devices that are limited to movement actuator, colour changer/optical output, smell generator, thermal output, and sound. These devices lack vestibular output and gustatory output. These devices also lack defined mechanisms of all sensory input: auditory, gustatory, kinesthetic, olfactory, tactile, vestibular, and visual input. These devices are primarily applicable to telephonic communications, in particular, mobile or cordless telephone messaging technology. A sensory output device includes a control means responsive to episodic receipt of data signals and/or emotional representation (emoticon).

Yet all of the sensory devices and devices heretofore known suffer from a number of disadvantages:

(a) The sensory devices in present use are limited in application.

(b) The sensory devices in present use are expensive to manufacture.

(c) The tests are limited by methods of identification of subject.

(d) The tests are limited by input device, display device, functionality, modality, dimensionality, and test type.

(e) The tests do not fully and automatically integrate incapacitated individuals, such as those with at least one of severe auditory, cognitive, neuromuscular, oral, visual, or other impairments. Such examinees preclude testing intraditional settings and even certain automated settings.

(f) The tests do not fully and automatically integrate those with lingual differences. Such examinees may require translators thereby increasing wait time, test time, test cost, and even scoring and analysis times and costs.

(g) The tests are not designed to fully integrate a variety or plurality of automatic sensing devices.

(h) The sensing devices are not manufactured for testing and/or evaluating applications. For example, a sensing device developed for telecommunication and text messaging is limited in scope and use.

These and other limitations of the prior art are overcome by our enhanced automatic apparatuses, methods, and systems.

No other measurement and evaluation tool known in the art offers an option to use at least one sensory input device, sensory output device, or sensory input device and sensory output device in automatic systems, methods, and apparatuses designed to measure and evaluate the masses.

U.S. Pat. No. 8,016,416 B1 (2011) describes automatic system and methods for measuring and evaluating at least one of mass vision, cognition, knowledge, operation skills, and the like and is therefore capable of objective, rapid, and uniform testing. When coupled with an integration of sensory devices, more efficient, economical, rapid, sophisticated, and thorough testing, evaluating, and identifying are accessible to the masses.

Ultimately, such enhancements improve safety and security and further empower those with physical inabilities and limitations. They also allow for the automatic assessment of sensation and physical properties, among other options.

Although sensory input devices provide satisfactory mechanisms for providing physical inputs to a processing system, and sensory output devices provide a satisfactory mechanism for offering physical outputs to a processing system, these devices are not necessarily always aesthetically pleasing. Thus, mechanisms that would provide options to improve usability, appearance, and performance have the potential to improve the user experience with the input device and/or output device, even apart from adding functionality.

Accordingly, this disclosure identifies new configurations for use in input devices and output devices that provide functionality and appearance options beyond those available in current automatic apparatuses, methods, and systems.

SUMMARY

In accordance with one embodiment, sensory input devices and sensory output devices comprise particularly, but not exclusively, devices for use with at least one of automatic systems, methods, or apparatuses for at least one of mass measurement, evaluation, and communication.

DRAWINGS

Figures

In the drawings, closely related figures have the same number but different alphabetic suffixes.

FIG. 1A illustrates a depiction of an embodiment of sensory input, sensory output, and automatic systems and methods of measuring and evaluating at least one of vision, cognition, operation skills, physical property, sensation, or the like;

FIG. 2A illustrates another depiction of an embodiment of sensory input, sensory output, and automatic systems and methods of measuring and evaluating at least one of vision, cognition, operation skills, physical property, sensation, or the like;

FIG. 2B illustrates an embodiment of a block diagram of operational components;

FIGS. 3A-3C show an embodiment of a flowchart of automatic systems and methods;

FIG. 4 shows an embodiment of a flowchart of an operation of steps for administering a vision test sequence.

DETAILED DESCRIPTION OF PREFERRED EMBODIMENTS

Figure 1A:
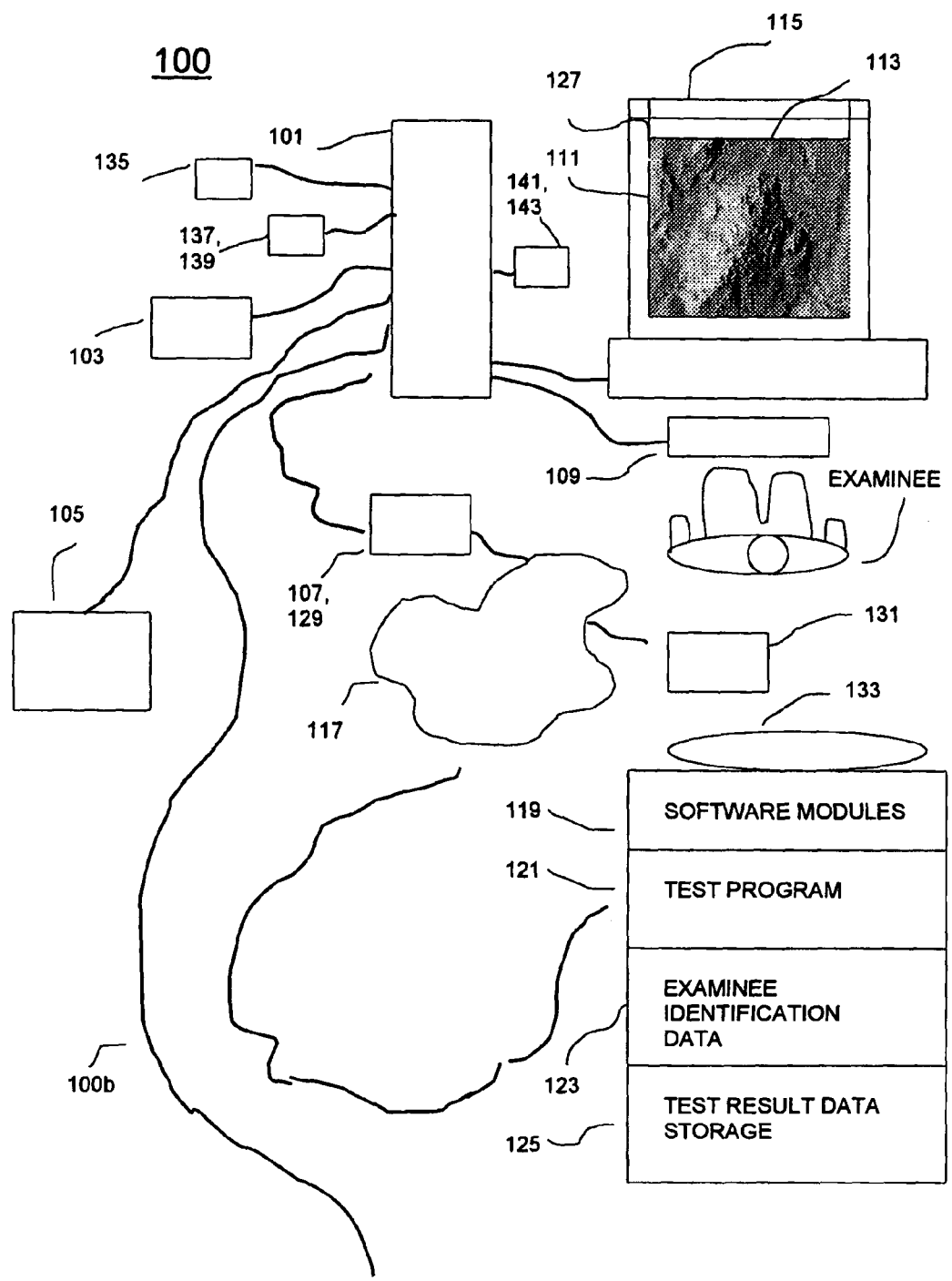

The following detailed description refers to the accompanying drawings that depict various details of examples selected to show how particular embodiments may be implemented. The discussion herein addresses various examples of inventive subject matter at least partially in reference to these drawings and describes the depicted embodiments in sufficient detail to enable those skilled in the art to practice without specific details. Many other embodiments may be utilized for practicing inventive subject matter than the illustrative examples discussed herein, and many structural and operational changes in addition to the alternatives specifically discussed herein may be made without departing from the scope of inventive subject matter. Still further, it should be understood that there are many alternate forms of embodiments. In addition, any suitable size, shape or type of elements or materials could be used. Structures and devices are shown in block diagram form in order to avoid obscurement.

References throughout this specification to "one embodiment" or "an embodiment," or to "one example" or "an example" mean that a feature being referred to is, or may be, included in at least one embodiment or example herein. Separate references to "an embodiment" or "one embodiment" or to "one example" or "an example" in this description are not intended to necessarily refer to the same embodiment or example; however, neither are such embodiments mutually exclusive, unless so stated or as will be readily apparent to those of ordinary skill in the art having the benefit of this disclosure. Thus, the present disclosure includes a variety of combinations and/or integrations of the embodiments and examples described herein, as well as further embodiments and examples as defined within the scope of all claims based on this disclosure, as well as all legal equivalents of such claims. Systems, methods, and apparatuses described herein may, therefore, take different forms, apply to various applications, and integrate into other devices.

For the purposes of this specification "computing device," "computing system," "processor-based system" or "processing system" includes a system that uses one or more processors, microcontrollers and/or digital signal processors and that has the capability of running a "program." As used herein, the term "program" refers to a set of executable machine code instructions, and as used herein, includes user-level applications as well as system-directed applications or daemons, including operating system and driver applications. Processing systems can include communication and electronic devices, such as mobile phones (cellular or digital), music and multi-media players, electronic reading device, and Personal Digital Assistants (PDA); as well as computers, or "computing devices" of all forms (desktops, laptops, servers, palmtops, workstations, tablet devices, notebooks, netbooks, etc.).

Reference to "senses" include balance (vestibular sense), hearing (auditory sense), motion (kinesthetic sense), sight (visual sense), smell (olfactory sense), taste (gustatory sense), and touch (tactile sense, skin sense, or haptic sense). The tactile senses are further divided into four separate senses since touch involves four different sets of nerves: cold, heat, pressure, and pain (nociception). Thermoception further defines a sense of temperature. Body awareness, sense of proprioception, constitutes a kinesthetic sense. Proprioception defines a sense and an awareness of the orientation of the body in space, the direction, extent, movement, position, and rate of the limbs, and the sense of muscular tension.

Electrodes may be used to stimulate, among others, at least one of physical property, sensation, or any combination there of. Examples of electrical stimulation procedures include electroconvulsive therapy (ECT), magnetic stimulation repetitive transcranial (rTMS) and vagal nerve stimulation (VNS). Deep brain stimulation (DBS) also delivers electrical stimulation to regions deep in the brain. Hence electrical stimulation is often used to stimulate muscle activity, initiate pain, relieve pain, produce sensation, or any combination thereof.

Sensation defines any operation, any function, and/or any perception of at least one of auditory sense, gustatory sense, kinesthetic sense, olfactory sense, tactile sense, vestibular sense, visual sense, or any combination thereof. Sensation also defines any awareness of stimuli through said senses. Sensation may also define a physical feeling or a mental condition that results from a said sense stimulation or from bodily change thereof.

A sensor measures a quantity to be controlled. Acceleration sensors, acoustic sensors, angle sensors, automotive sensors, chemical sensors, density sensors, displacement sensors, distance sensors, electric current sensors, electric potential sensors, environment sensors, flow sensors, fluid velocity sensors, force sensors, Global Positioning System (GPS), heat sensors, humidity sensors, ionizing radiation sensors, imaging sensors, inclinometer, level sensors, light sensors, linear displacement sensor, Linear Variable Differential Transformer (LVDT), liquid level transducers, magnetic sensors, mechanical sensors, microphone, microswitch, moisture sensors, navigation instrument sensors, optical sensors, photon sensors, position sensors, presence sensors, pressure sensors, proximity sensors, radar altimeter, rotary displacement sensor, radio sensors, shaft encoder, sound sensors, speed sensors, strain gauge, subatomic particle sensors, tachometer, temperature sensors, thermal sensors, vibration sensors, tilt sensor, and weather sensors are some of many examples of sensors.

Sensors are used to sense at least one of auditory, chemical, electrical, gustatory, kinesthetic, mechanical, olfactory, tactile, vestibular, and/or visual phenomena.

Sensory feedback also serves as at least one of an indication of disease state, responsiveness to therapy, determination of treatment parameters, or any combination thereof. As an example, neural response to intracranial stimulation in the form of sensory feed back optimizes control of movement disorders and other neurological disease, as identified in Dilorenzo (U.S. Pat. No. 6,819,956). Examples of sensory feedback include but are not limited to at least one of electromyographic signals, accelerometers, electrodes, acoustic transducers, force sensors, pressure sensors, velocity sensors, neurotransmitter sensors, chemical sensors, or any combination thereof. Neural response, another example of sensory feedback (when used to assess mental state of a subject), serves as an indication of neurological disease state, therapy response, and/or treatment determination.

Identification of an examinee today may include at least one of bodily part recognition (such as identification by patterns in at least one of a brain, muscular system, nervous system, organ (eye, ear, heart, liver, lungs), density or structure of bones of the head, body, arms, legs, or vertebra), bodily fluid recognition (such as saliva or other bodily liquids), biological recognition (such as blood or tissue), chemical recognition (such as perspiration, bodily scents, bodily chemicals, or pheromones), bodily temperature recognition (such as specific heat measurements), bodily touch recognition (such as a calculated tap sequence), genetic marker recognition (such as DNA or RNA), dental recognition (such as the structure, patterns, and distinct markings of teeth), personal data (such as information that is specific only to an examinee, such as a special password, birth date, birthplace, address, and maiden names of an examinee or a relative of an examinee), or any combination thereof.

A sensory device is a device that performs at least one of detection, measurement, processing, simulation, or stimulation of the senses of an individual. Such a device may operate as a form of a response to stimuli. Examples of sensory devices include but are not limited to sensory input device and sensory output device. Sensory devices are responsive to data signals, among others, to provide sensory stimuli, sensory responses, sensory input, and/or sensory output.

Generally, sensory output includes but is not limited to vestibular output, auditory output, kinesthetic output, visual output, olfactory output, gustatory output, and tactile output, Tactile output may further include thermal output, such as cold output and/or heat output, pressure output, and nociception output. Thermoception output and proprioception output are additional examples of sensory output. Sensory output devices include but are not limited to wearable items, three dimensional objects such as pebbles, ornaments, toy characters, and/or the like. Yet, throughout this reference, a printer may also illustrate, as an example, a form of a sensory output device since its output is visual and it may require a combination of tactile, visual, and/or auditory senses to utilize. For example, a brail printer is sensory in nature as it requires touch to read. Eye-read printers are also a form of sensory output that require the sense of sight to read.

Sensory input devices are those devices that allow the input of vestibular input, auditory input, kinesthetic input, visual input, olfactory input, gustatory input, and tactile input, Tactile input may further include thermal input, such as cold input and/or heat input, pressure input, and nociception input. Thermoception input and proprioception input are additional examples of sensory input.

An actuator affects a system to be controlled. An actuator may activate, move, or control a mechanism, system, or any combination thereof. An actuator, as an example, may activate a mechanical device, such as one connected to a processor by a sensor link. Actuator interfaces, for example, may couple to sensory output, sensory input, or any combination thereof to activate such mechanisms. Other examples of actuators include but are not limited aircraft control surfaces, electric, electricmotors, heaters, hydraulic, piezo-electric transducer, pneumatic, pumps, solenoid, voice coil, among others.

Mnemonic defines any device and/response, such as a pattern of letters, ideas, or associations, and/or technique, that aids in memory and/or memorization.

Telemetry defines any automatic data transmission and measurement from remote sources by wire, radio, and/or other means.

Telepathy defines any communication of thoughts, feelings, or ideas by means other than the known senses.

Biometric identification includes but is not limited at least one of voice print recognition, facial recognition, finger print recognition, hand writing recognition, pattern of finger lengths recognition, retina recognition, iris recognition, or any combination thereof.

Body circulation includes but is not limited to vein pattern characterization.

Bodily motion recognition includes but is not limited to a foot print sound, movement, tapping, tick, or any combination thereof.

Bodily sound includes but is not limited to voice, voice recognition, and/or any sound emitted and/or thought.

Bodily temperature includes but is not limited to thermal pattern characterization.

An oral condition is one that impacts at least one of the spoken words, thoughts, ideas, or speech of an individual.

A linguistic condition is one that impacts at least one of the language or use of tongue of an individual.

Physical property describes and includes but is not limited to any physical measure, description, feature, ability, and/or characterization of a body. This may include measures and/or characterization such as head-neck flexibility, leg strength, and general mobility, heart rate, brain function, arm strength, hand strength, foot strength, phalanges strength, reaction time, mouth strength, back strength, strength of senses, among others. Physical property may also define a limb, an organ (such as a lung, heart, etc.), or any other part of a body. Physical property may also define any property used to characterize a physical feature, condition, injury, and/or disease to a body.

Calculated measurements use any kind of imagery of an eye and/or other part of the body to assess a condition.

A wireless controller, can be used as a handheld pointing device and detects movement in three or more dimensions.

There are numerous methods, instruments, and systems designed to screen or test cognition. One of the oldest and most commonly administered cognitive tests, among many other traditional tests, are the Trail Making Test Part A, the Trail Making Test Part B, and the Clock Drawing Test. Trail Making Test Part A and Trail Making Test B are commonly referred to as the Trail Making Tests. Trail Making Test Part A is a timed test that requires the connection of a sequence of calculated numbers. Trail Making Test Part B is a timed test that requires the connection of calculated numbers and calculated letters in an alternating sequence. Trail Making Test Part B is considered more complex than Trail Making Test A. Trail Making Tests, commonly distributed on paper yet now widely available in automated and online versions such as Automatic Trail Making Test™ Part A, Automatic Trail Making Test™ Part B, Automatic Trail Making Tests™ (all manufactured by Specialty Automated Corporation™) may integrate other symbols and features into a trail. For example, there may be a trail of sensory characterization, such as one that incorporates input and/or output of auditory sense, gustatory sense, kinesthetic sense, olfactory sense, tactile sense, vestibular sense, and/or visual sense phenomena and/or elements. Chemical, electrical, and/or mechanical elements may also be incorporated into such tests.

Trail Making Tests are used to measure and evaluate at least one of attention, calculation, executive function, impulsivity, memory, memory recall, mental flexibility, orientation, psychomotor speed, task switching, visual scanning, visual search, visual attention, or motor speed, among others.

Clock Drawing Tests are also widely used cognitive screening tools that present a menu of time-related queries associated with at least one of a blank page, a pre-drawn circle, a pre-drawn clock, or any combination thereof. While commonly administered on paper and with a pencil, and scored manually, there are automated versions, such as Automatic Clock Drawing Test™, Automatic Military Clock Drawing Test™, (all manufactured by Specialty Automated) that provide fully automated, objective, autonomous, uniform, and rapid testing.

Other known cognitive tests may include but are not limited to Boston Naming test, Controlled Oral Word Association (COWA) test, Rey Auditory Verbal Learning Test (RAVLT), WAIS-III, Wechsler Adult Intelligence Scale, Wechsler Memory Scale, WMS-III, MMPI, and/or Stroop.

Information data uniquely define each examinee according to calculated measures, senses, and characteristics. Information data includes but is not limited to biometrics, thermal imaging, radio frequency identification (RFID tags), brain scans, or the like.

Embodiments of automatic systems, apparatuses, and methods that measure and evaluate at least one of vision, cognition, operation skills, sensation, physical property, or the like are presented herein.

It will be appreciated that a preferred embodiment may be readily implemented in any form that executes automation. This includes software that may be used on a variety of hardware platforms. Alternatively, the disclosed system may be implemented partially or fully in hardware using standard logic circuits. Whether hardware, software, or any other form that executes automation is used to implement the system varies depending on the speed and efficiency requirements of the system, the particular function of such systems, and the particular systems, such as microprocessor or microcomputer systems.

In the first illustration, for example, we may assume that the unitary housing encompasses comprehensive screening including all elements of a vision test, cognition test, knowledge test, operation skills test, physical property test, and sensation test. However, a client may only require one kind of screening, such as a vision test. In this case, there may only then be a requirement for system initialization, vision test instructions, vision test administration, vision test completion protocol, and vision test result data processing and output. Such input and/or output may be physical property—even in the absence of a physical property test.

Although a preferred embodiment is shown for use with one system, it should be clearly understood, that use with other computerized systems, methods, devices, simulators, and/or stimulators, are integrable systems and/or related devices that may be connected locally, remotely, wirelessly, through a thin client, and/or any other means for data exchange, transmission, and sharing. Thin clients, for example, save space and may be ergonomically and economically feasible for places such as transportation bureaus, homes, medical facilities, security agencies, militaries, or the like. Since a thin client performs most of its processing on a central server or at some centralized managed site, very little hardware and software are usually required at the examinee's location.

Still further, it is obvious to those skilled in the art that embodiments of block schematic diagrams of a control circuit (FIGS. 9 to 11) for at least one of a sensory input device, sensory output device, or any combination thereof apply to communications, and, in particular, telecommunications.

When there are no disorders detected through any automatic tests, the examinee may be notified through at least one of automatic output, sensory output, optional output, physical property output, or passing scores on tests completed, or any combination thereof. Examples of sensory output may include auditory output, gustatory output, kinesthetic output, olfactory output, tactile output, vestibular output, and visual phenomena output, or any combination thereof. Electrical output, mechanical output, chemical output, or any combination thereof are examples of optional output.

Figure 1B:
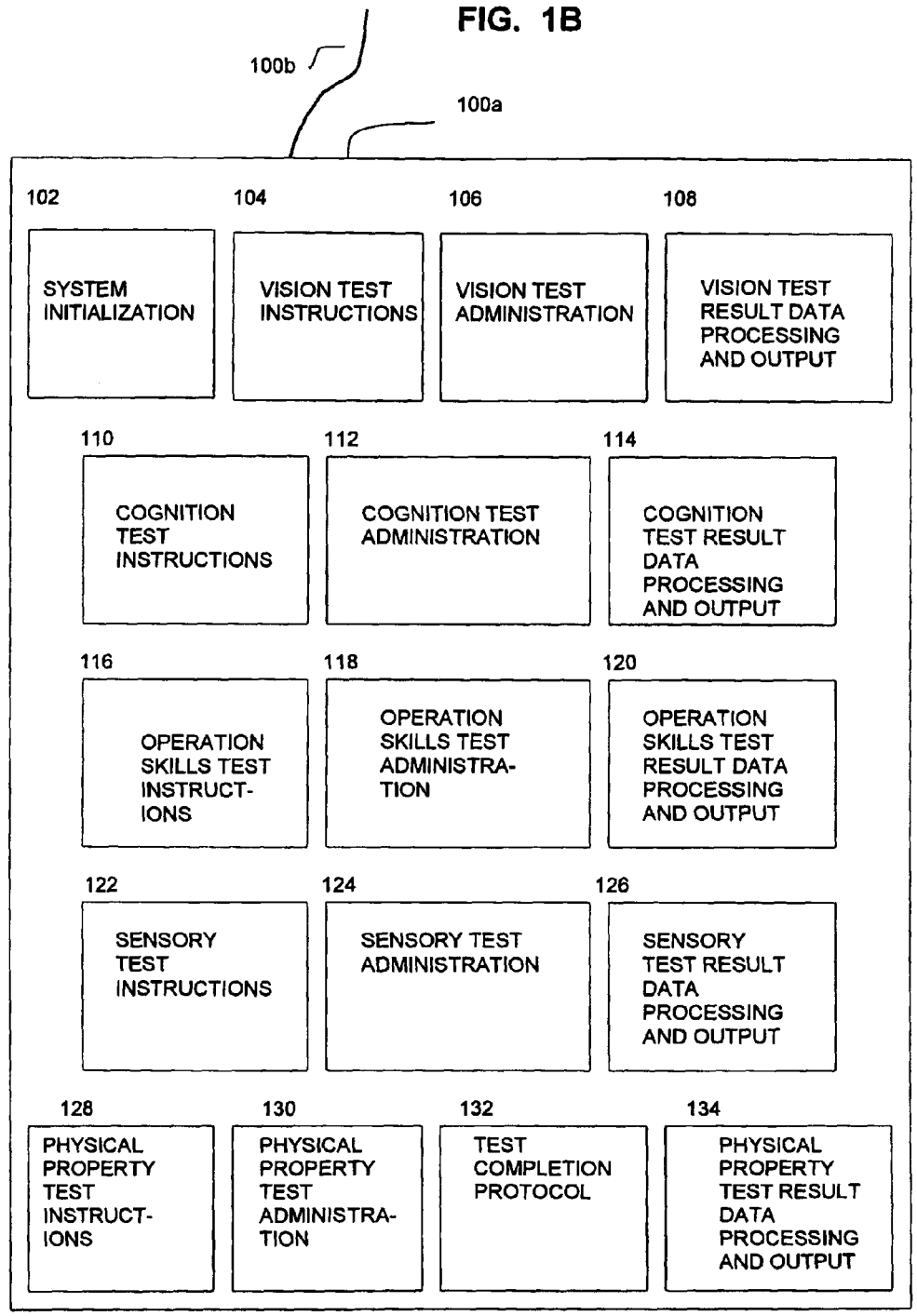
FIG. 1B illustrates an embodiment of a block diagram of operational components.

System 100 is illustrated in FIGS. 1A and 1B. System 200 is presented in FIGS. 2 A and 2 B. In FIGS. 3 A, 3 B, 3 C, 4, 5, 6, 7, and 8, flow charts are shown for various elements of a System 100 and/or System 200.

FIG. 1A illustrates, in schematic block diagram, an example of the system 100, including any interconnected network for data transmission, sharing, and exchange, 117, such as an Internet, Intranet, Extranet, or the like, independent of location. Instruction data may be displayed. An examinee is positioned at a calculated distance in front of a display device 127. In this embodiment, there is one display device. However, in order to provide a more realistic view of features such as those inherent to certain tests (for example, a road for a driving test), among others, for such tests as operation skills, vision, sensation, physical property, or certain cognition tests, more than one display device may be incorporated. To authenticate, establish, update, or modify the identification of an examinee, which is generally necessary when screening tests of the masses are performed, a user identification input device, 103, based on information data input can be used. Information data may include but not be limited to any means for identifying an examinee, such as biometrics, thermal imaging, radio frequency identification (RFID tags), or the like. Such information can be stored or retrieved through an examinee identification data 123. Examinees connect to the system 100 through the use of a communications device or connection device such as a modem 107 or a connection device, such as a computer network interface card 129 installed in a device that accepts information in digital or similar form and manipulates it for a result based on a sequence of instructions, such as a computer 101 or the like. A displaying device, such as a computer program used for accessing sites or information on a network, or standard browser 115, such as Netscape Navigator®, Firefox® Google Chrome®, Apple Safari®, or Microsoft Internet Explorer®, can be used to remotely access a group of electronic pages generally connected to one another, such as a website 131 established by a device that provides information and services, such as the server(s) 133. However, the system can consist of any integrable displaying device. Website 131 preferably includes the use of text, digital images, audio and/or video, developed using conventional software tools and languages, such as ActiveX technology, C++, Java, and/or HTML, among others.

An examinee can respond to observed test stimuli. The system comprises user input device(s), 109, such as at least one of a physical property device. X-ray, physical measure device, hologram, computer mouse, wireless mouse and pad, keyboard, touch screen, joystick, brake pedal, accelerator pedal, pedal, steering wheel, microphone, camera, horn, virtual reality device, control device fitted with motion sensors, interactive screen, electronic display, or any other device capable of detecting an individual's response to testing stimuli.

Various programmable electronic devices that can store, retrieve, and process data, such as automated and computerized screening tests, can be provided to an examinee using an automated viewer used to access an interconnected network for data sharing and exchange, such as a browser 115, including, for example, unaided cognitive tests, vision tests, operation skills tests, sensory tests, and physical property tests, among others. Such automatic tests can be readily stored on devices that execute automation, such as portable software modules 119, such as Java applets, and than downloaded and executed locally on user's computer 101, or, alternatively, executed on a computer or plurality of computers located at a central facility. Each device that executes automation, such as software module 119 tests for at least one of desired visual, cognitive, operation skills, sensory, physical property, or related deficiency by displaying to an examinee test stimuli, such as 113, of different color, contrast, frequency, location, shape, size, speed, sensation, and/or intensity on a display device, such as monitor 127, and then by recording and comparing what the user reports seeing with what is presented by a device that accepts information in digital or similar form and manipulates it for a result based on a sequence of instructions, such as a computer 101. A calibration program (not shown) may be needed to calibrate display devices, such as monitors of various sizes.

Computer(s) in a network may provide(s) services to other computers in a network, such as server(s) 133, include screening test program(s) 121 incorporated into module(s), such as software 119. An operating system executes a test program 121 when a test is to be conducted. A test program(s) measure(s) an examinee's visual, cognitive, sensory, physical property, and/or operation skills capabilities and/or conditions. These tests, as generally defined in 100a of FIG. 1B, include elements of program(s) of the system(s) that implement algorithms for, among other operations, initialization of the system 102, vision test instructions for a test examinee 104, vision test administration 106, vision test result data processing and output 108, cognition test instructions for a test examinee 110, cognition test administration 112, cognition test result data processing and output 114, operation skills test instructions 116, operation skills test administration 118, operation skills test result data processing and output 120, sensory test instructions for a test examinee 122, sensory test administration 124, sensory test result data processing and output 126, physical property test instructions for a test examinee 128, physical property test administration 130, physical property test result data processing and output 134 and test completion protocol 132. While connected to computer 101, they may also be directly connected to some remote server. The actual algorithms for each operation, examinee identification, and/or any that may be required for a calibration program (to determine the physical pixel size of display monitor 127 to keep stimuli of the same pixel size the same physical size) being structured in a manner as would be understood by one of skill in the art.

Test stimuli 113 are represented by any of the small discrete elements that together constitute an image, such as pixels, and may be transmitted from a video controller (not shown) within computer 101 or through server(s) 133 to display device, such as monitor 127 having a viewable area 111 representing the surface where the pixels are output. Computer 101 monitors an examinee's response, which is entered by, preferably, the employ of a user input device 109. It also displays test stimuli 113. (This image is provided courtesy of NASA.)

Once an examinee's test scores or results are available, these may appear on a display device 127 or through use of an output device, 105, such as a printer, via test result data storage 125. A printer may also illustrate, as an example, a form of a sensory output device. Still further, a printer may also represent an output device that processes, prints, replicates, creates, stores, and/or generates output of at least one of predetermined dimensionality, predetermined geometrical transformation, or the like. Connection 100b links 100a to a device that accepts information in a digital or similar form and manipulates it for a result based on a sequence of instructions, such as a computer, a processor, or the like 101. Sensory input device 137 couples to actuator interface 139 that connects to processor 101. Location sensor 135 allows actions to vary from place to place. Actuator interface 141 couples to sensory output device 143.

Figure 2A:
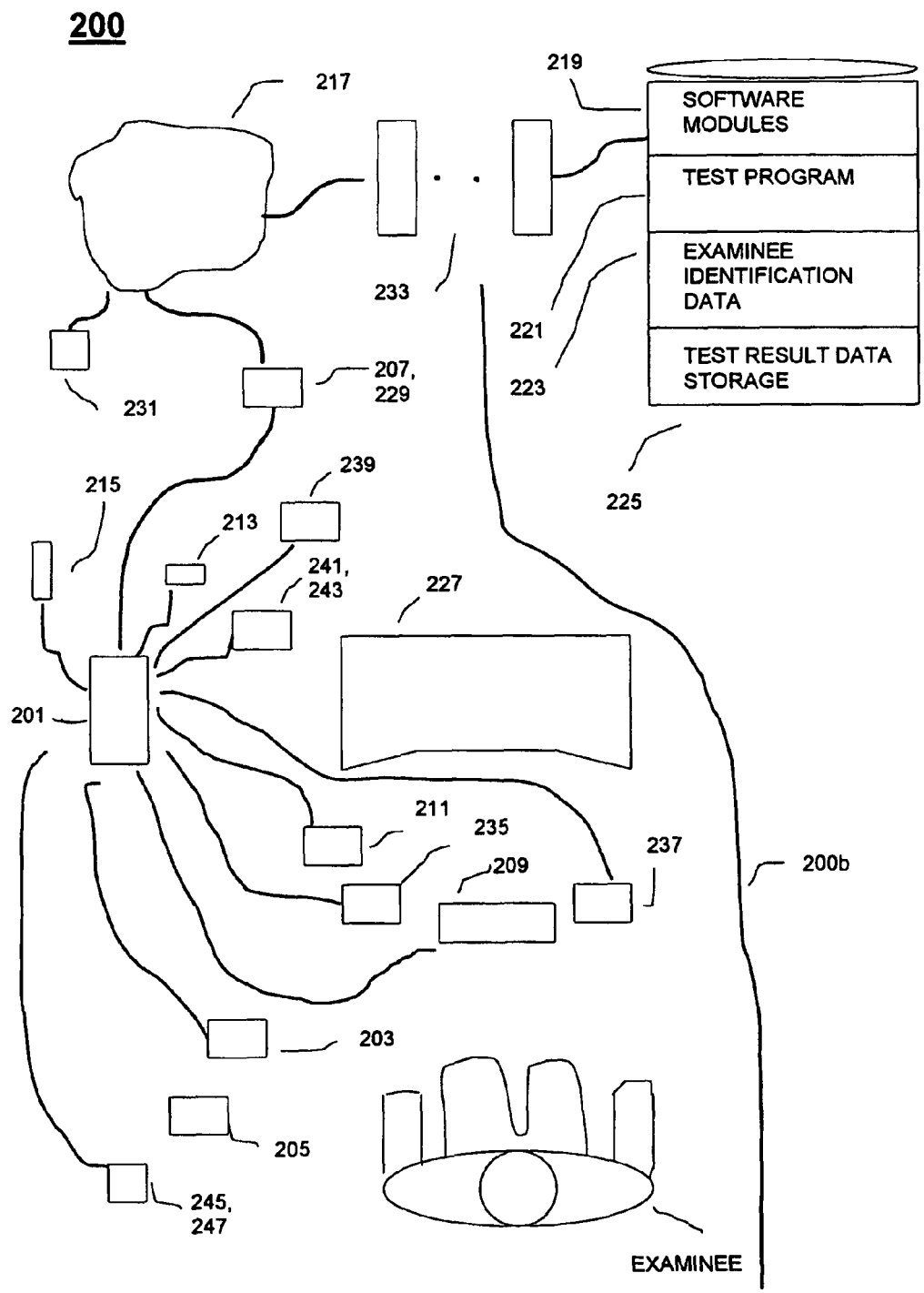

FIG. 2A depicts a schematic block diagram, at least one example of a system 200, including an interconnected network for data sharing and exchange, 217, such as the Internet, Intranet, or Extranet. An examinee is positioned at a fixed distance in front of a display device, such as a monitor 227. In this embodiment, for example, there are multiple display devices, such as three monitors, which are generally preferred to provide a more realistic view of features such as roads, for such tests as operation skills, vision, or certain cognition tests. However, at least one display device, such as a monitor, may be incorporated. To authenticate, establish, update, or modify the identification of an examinee, which is generally necessary when testing of the masses are performed, a user identification input device, 203, based on information data input, such as biometrics, thermal imaging, radio frequency identification (RFID tags), or the like can be used. Such information can be stored or retrieved through examinee identification data 223. Examinees connect to the system 200 through the use of a communications device or connection device such as a modem 207 or a connection device, such as a computer network interface card 229 installed in a device that accepts information in digital or similar form and manipulates it for a result based on a sequence of instructions, such as a computer 201 or the like. A displaying device, such as a computer program used for accessing sites or information on a network, or standard browser 215, such as Netscape Navigator®, Firefox®, Google Chrome®, Apple Safari®, or Microsoft Internet Explorer®, can be used to remotely access a group of electronic pages generally connected to one another, such as a website 231 established by a device that provides information and services, such as server(s) 233. However, the system can consist of any integrable displaying device. Website 231 preferably includes the use of text, digital images, audio and/or video, developed using conventional software tools and languages, such as ActiveX technology. C++, Java, and/or HTML, among others. Audio output devices 235 and 237 may constitute a conventional sound card with speakers, all as known in the art.

An examinee can respond to observed test stimuli with the aid of user input device(s), 209, such as at least one of an accelerator pedal, brake pedal, camera, computer mouse, hologram, horn, joystick, keyboard, physical measure device, microphone, physical property device, sensor, sensory device, sensory input device, steering wheel, telepathic input device, touch screen, video device, virtual reality device, wireless mouse and pad, X-ray, control device fitted with motion sensors, interactive screen, any other device capable of detecting an individual's response to testing stimuli, or any combination thereof. In this example, the setup is similar to that of a desktop driving simulator. Therefore, a user input device 211, such as an accelerator and/or brake pedal, can be included.

Various programmable electronic devices that can store, retrieve, and process data, such as automated and computerized screening tests, can be provided to an examinee using an automated viewer used to access an interconnected network for data sharing and exchange, such as browser 215, including, for example, unaided cognitive tests, vision tests, operation skills tests, sensory tests, and physical property tests, among others. Such automatic tests can be readily stored on devices that execute automation, such as portable software modules 219, such as Java applets, and then downloaded and executed locally on user's computer 201, or, alternatively, executed on a computer or plurality of computers located at a central facility. Each device that executes automation, such as software module 219 tests for at least one of desired vision, cognition, operation skills, sensation, physical property measures related deficiency by displaying to an examinee test stimuli, such as 213 of different color, contrast, frequency, location, shape size, speed, and/or intensity on a display device, such as monitor 227, and then by recording and comparing what the user reports seeing with what is presented by computer 201. A calibration program (not shown) may be needed to calibrate display devices, such as monitors, of different sizes.

Server(s) 233 include screening test program(s) 221 incorporated into module(s), such as software 219. An operating system executes test program 221 when a test is to be conducted. A screening test programs) measure(s) an examinee's visual, cognitive, sensory, physical properties, and/or operation skills capabilities and/or conditions. These tests, as generally defined in 200a of FIG. 2B, include the elements of the program of the system that implement algorithms for, among other operations, initialization of the system 202, vision test instructions for a test examinee 204, vision test administration 206, vision test result data processing and output 208, cognition test instructions for a test examinee 210, cognition test administration 212, cognition test result data processing and output 214, operation skills test instructions 216, operation skills test administration 218, operation skills test result data processing and output 220, sensory test instructions for a test examinee 222, sensory test administration 224, sensory test result data processing and output 226, physical property test instructions 228, physical property test administration 230, physical property test result data processing and output 234 and test completion protocol 232. While connected to computer 201, they may also be directly connected to a local network, a plurality of networks, a plurality of servers, a local computer, or the like. Actual algorithms for each operation, examinee identification, and/or any that may be required for a calibration program (such as one to determine the physical pixel size of display monitor 227 to keep stimuli of the same pixel size the same physical size) being structured in a manner as would be understood by one of skill in the art.

Test stimuli 213 are represented by any of the small discrete elements that together constitute an image, such as pixels, and may be transmitted from a video controller (not shown) within computer 201 or through servers) 233 to display monitor 227 having a viewable area representing the surface where the pixels are output. Computer 201, a processor, monitors an examinee's response, which is entered by, preferably, the use of a user input device 209. It also displays test stimuli 213.

Once an examinee's test scores or results are available, these may appear on a display, device, such as a monitor 227 or through use of an output device, 205, such as a printer, via test result data storage 225, and/or a sensory device. A printer may also illustrate, as an example, a form of a sensory output device. Still further, a printer may also represent an output device that processes, prints, replicates, creates, stores, and/or generates output of at least one of predetermined dimensionality, predetermined geometrical transformation, or the like. Connection 200b links 200a to a device that provides information and services, such as server(s) 233.

Sensory input device 241 couples to actuator interface 243 that connects to processor 201. Location sensor 239 allows actions to vary from place to place. Actuator interface 245 couples to sensory output device 247.

Figure 3A:
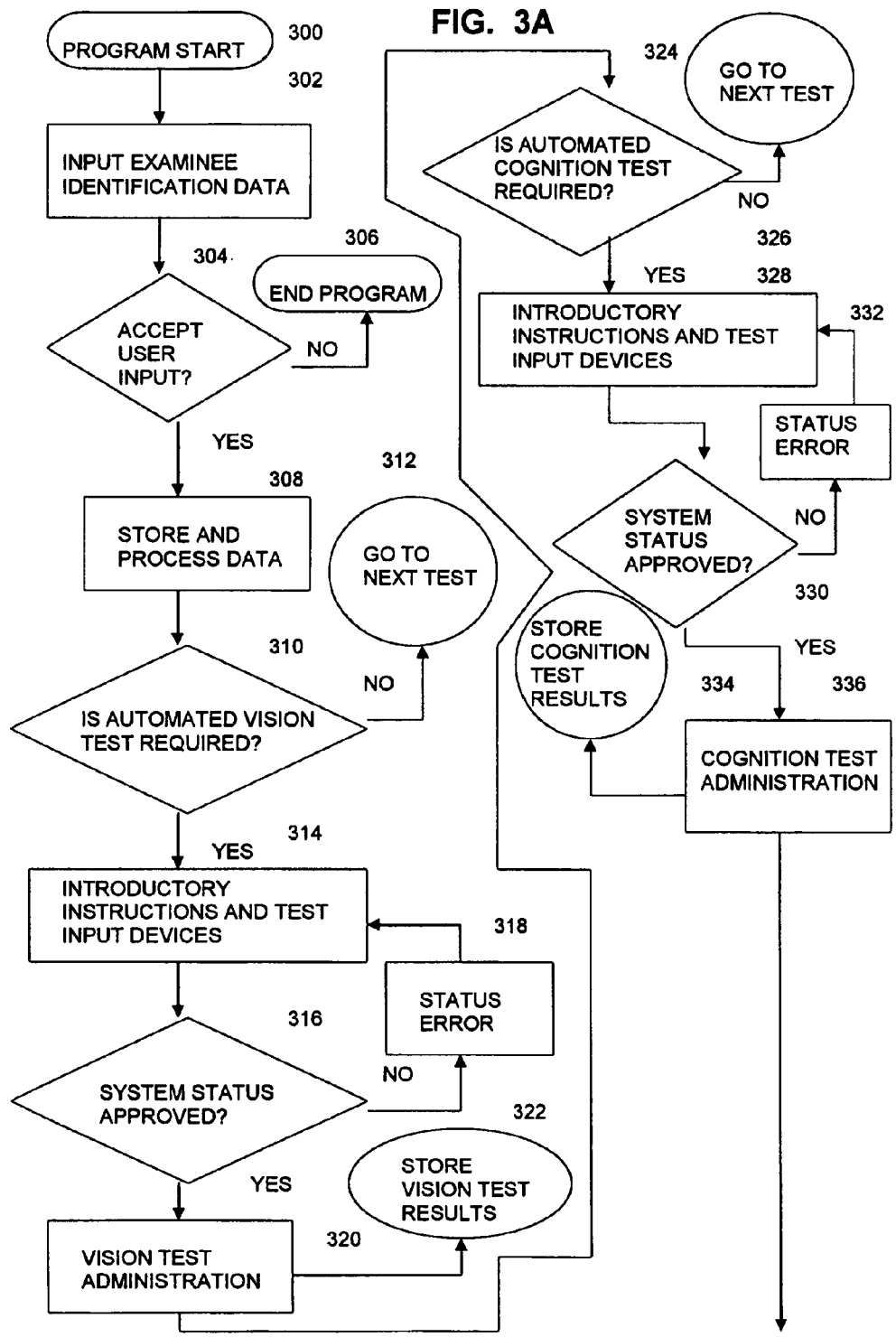

Referring to FIG. 3A, shown there is at least one embodiment of automatic systems, methods, and apparatuses, a flow chart of the general overall operation of a system. This depiction allows an examinee to take a series of tests, a vision test, a cognition test, an operation skills test, a sensory test, and/or a physical property test with an option of doing it all sequentially. This may or may not be performed on the same day, depending on test results as well as the preferences and schedules of an examinee. For example, since this is a unitary system comprised of at least one test, if an examinee successfully passes a vision test, an examinee may automatically proceed to a cognition test, an operation skills test, a sensory test, and/or a physical property test. Hence tests may be available in any desired sequence. For this illustration, however, a vision test precedes a cognition test, which precedes an operation skills test, which precedes a sensory test, which precedes a physical property test. Introductory instructions may include audio, video, text, images telepathy, sensation, physical property, or any combination thereof to aid the examinee. Sample questions may or may not be provided. Introductory instructions may also include security screening and/or data collection and/or verification to ensure that the examinee who submits identification data is the same examinee who is being screened and/or tested. Such security screening and/or data collection and/or verification may also be incorporated randomly and/or uniformly, in each test and/or inquiry to ensure integrity.

At the start of each test, it is recommended to test input devices for correct settings.

Improper use and/or condition of input devices may cause a rejection of a system status and an occurrence of a status error.

In this operation, for example, a system, such as System 100, begins (Step 300) with the prompting of an examinee for the input of identification data (Steps 302-304). A program ends (Step 306) if an examinee's identification data is rejected. As long as the identification data is accepted, an examinee's data is stored and processed (Step 308). An examinee is prompted to declare whether or not a vision test is required and/or desired (Step 310). An examinee reserves the option to proceed to the next test (Step 312). When an examinee indicates that a vision test is required (Step 310), introductory instructions are provided and input devices are tested (Step 314).

A system may determine if user input devices 109 are operational and if an examinee demonstrates an understanding of these devices based on input signals received when an examinee operates them. (An examinee is generally allowed the option to skip this section if desired because a system that is not functioning should be obvious to one skilled in the art.)

When a system status (Step 316) is rejected, which may be due to improper use or condition of the input devices, a status error appears (Step 318). Step 314 is repeated. When the system status is approved, particularly through a successful sweep of input devices and/or an examinee's use of these devices, vision test administration (Step 320) initiates. Vision test results are stored (Step 322). Such data may be stored in a test result data component 125. These may be available for review though output device 105.

In the next test sequence, a system proceeds with prompting an examinee to respond (Step 324) to whether or not an automated cognition test is required. An examinee has the option of proceeding to the next test (Step 326) if required and/or desired. Introductory instructions are provided and input devices are tested (Step 328). A system may determine if user input devices 109 are operational and if an examinee demonstrates an understanding of these devices based on input signals received when an examinee operates them. (An examinee is generally allowed the option to skip this section if desired because a system that is not functioning should be obvious to one skilled in the art).

When a system status (Step 330) is rejected, which may be due to improper use or condition of an input device, a status error appears (Step 332). Step 328 is repeated. When a system status is approved, particularly through a successful sweep of the input devices and/or an examinee's use of these devices, a cognition test administration (Step 336) initiates. Cognition test results are stored (Step 334). Data may be stored in a test result data component 125. These may be available for review though output device 105.

Figure 3B:
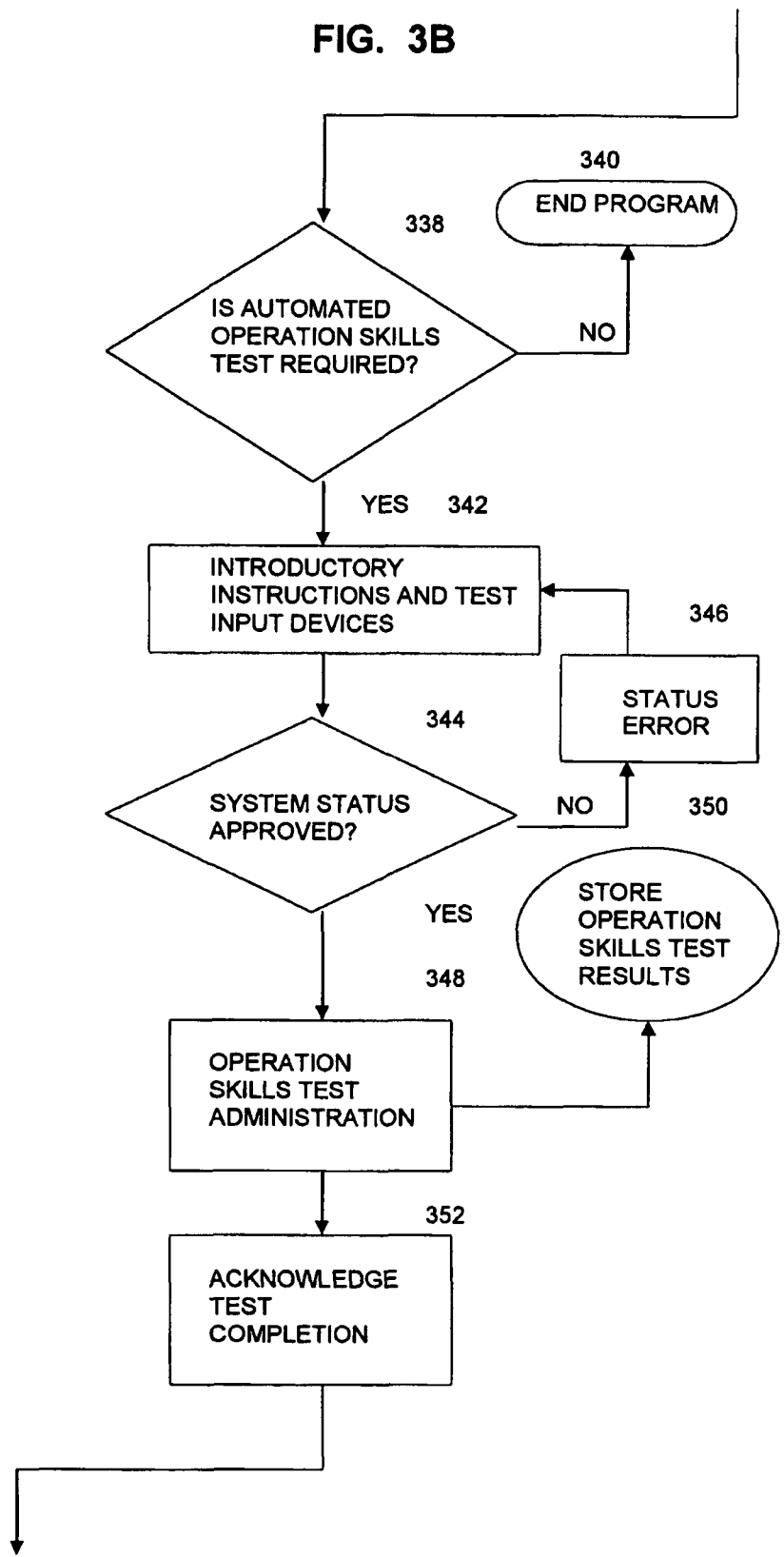

In the next test sequence, shown in FIG. 3B, a system proceeds with prompting an examinee to respond (Step 338) to whether or not an automated operation skills test is required. An examinee has the option to end a program (Step 340) if required and/or desired. Introductory instructions are provided and input devices are tested (Step 342).

A system may determine if user input devices 109 are operational and if an examinee demonstrates an understanding of such devices based on input signals received when an examinee operates them. (An examinee is generally allowed the option to skip this section if desired because a system that is not functioning should be obvious to one skilled in the art.)

When a system status (Step 344) is rejected, which may be due to improper use or condition of input devices, a status error appears (Step 346). Step 342 is repeated. When a system status is approved, particularly through a successful sweep of the input devices and/or an examinee's use of such devices, operation skills test administration (Step 348) initiates. Operation skills test results are stored (Step 350). Such data may be stored in a test result data component 125. These may be available for review though output device 105 and after test completion (Step 352).

In the next test sequence, the system proceeds with prompting an examinee to respond (Step 354) to whether or not an automated sensory test is required. There is an option of proceeding to the next test (Step 356) if required and/or desired. Introductory instructions are provided and input devices are tested (Step 358).

When a system status (Step 360) is rejected, which may be due to improper use or condition of the input devices, a status error appears (Step 362). Step 358 is repeated. When a system status is approved, particularly through a successful sweep of input devices and/or an examinee's use of these devices, a sensory test administration (Step 364) initiates. Sensory test results are stored (Step 366). Such data may be stored in a test result data component 125. These may be available for review though output device 105.

An examinee may proceed to a next test (Step 372) if an automated physical property test (Step 368) is not required. Introductory instructions are provided and input devices are tested (Step 370) if an automated physical property test (Step 368) is required.

When a system status (Step 374) is not approved, which may be due to improper use or condition of an input device, a status error (Step 376) appears. Step 370 is repeated. When a system status is approved (Step 374), particularly through a successful sweep of the input devices and/or an examinee's use of these devices, a physical property test administration (Step 378) initiates. Physical property test results are stored (Step 380). Such data may be stored in a test result data component 125. These may be available for review though output device 105. The program ends (Step 382).

FIG. 4 shows a flow chart for a specific operation of the steps for administering a vision test. In this operation, a system, such as System 100, begins (Step 400) with the prompting of an examinee for an input of identification data (Steps 401-402). A program ends (Step 403) if an examinee's identification data is rejected. Once said identification data is accepted, an examinee's data is stored and processed (Step 404).

A system proceeds with prompting an examinee to respond (Step 405) to whether or not a vision test is required. An examinee has the option of proceeding to a next test (Step 406) if a vision test is not required. Introductory instructions are provided and an input device is tested (Step 407) if a vision test is required.

A system may determine if user input devices 109 are operational and if an examinee demonstrates an understanding of these devices based on input signals received when an examinee operates them. A system may then determine if an examinee responds correctly (Step 408). An examinee who does not respond correctly will receive an output warning (Step 409) and repeat Step 407. (An examinee is generally allowed the option to skip this section if desired because a system that is not functioning should be obvious to one skilled in the art.)

When an examinee responds correctly (Step 408), vision test administration (Step 410) initiates. Vision test results are stored (Step 411). Such results may be stored in a test result data component 125. When an examinee responds correctly (Step 412), an examinee may proceed to a next test (Step 416). An output warning (Step 413) is issued to an examinee who does not respond correctly (Step 412). Test completion is acknowledged (Step 414) and a program ends (Step 415).

Figure 5:
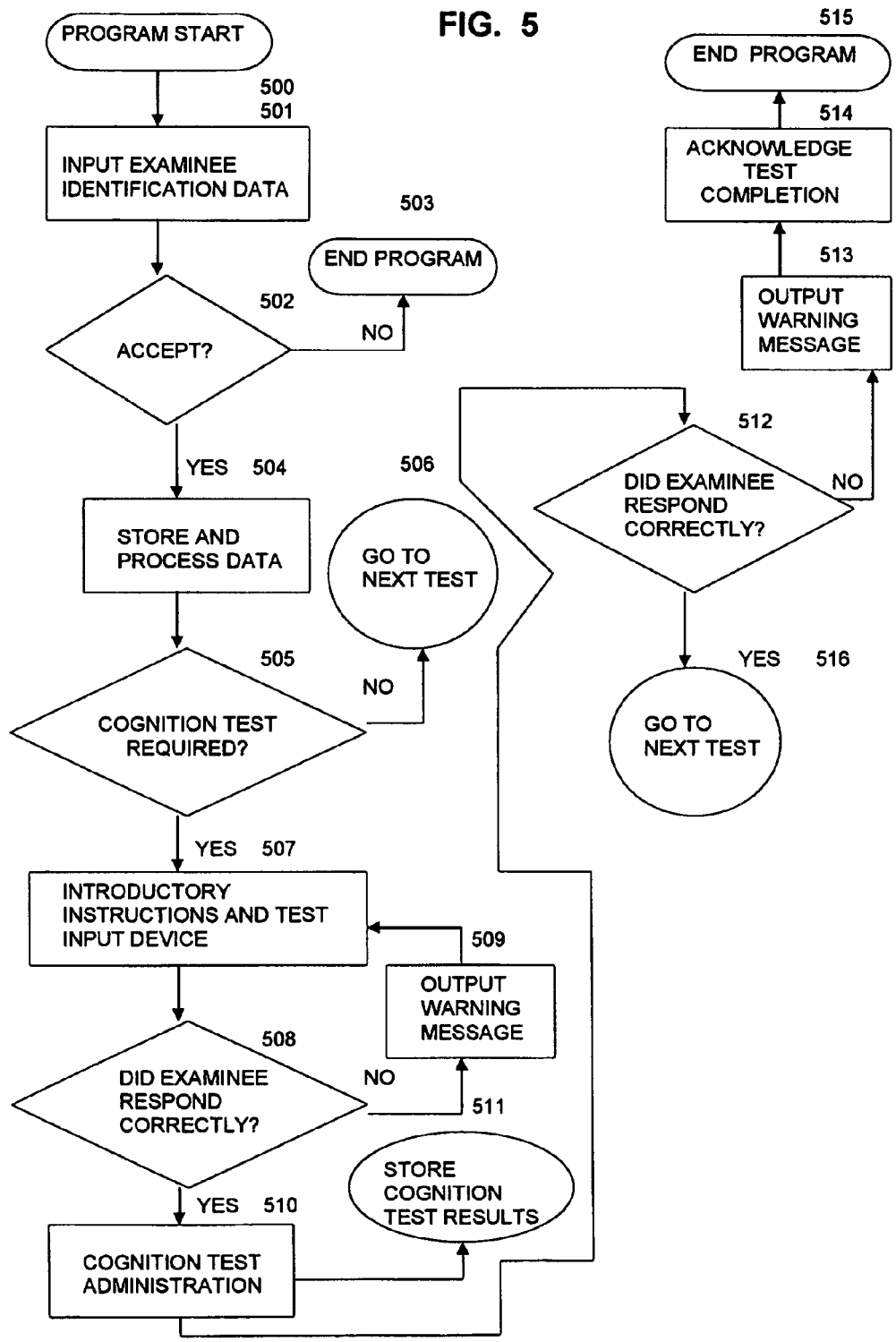
FIG. 5 shows an embodiment of a flowchart of an operation of steps for administering a cognition test sequence.

FIG. 5 shows a flow chart for a specific operation of the steps for administering a cognition test. In this operation, a program starts (Step 500) with the prompting of an examinee for the input of identification data (Steps 501-502). The program ends (Step 503) if an examinee's identification data is rejected. As long as the identification data is accepted, an examinee's data is stored and processed (Step 504). An examinee may proceed to the next test (Step 506) if a cognition test (Step 505) is not required.

A system proceeds with prompting an examinee to respond (Step 505) to whether or not an automated cognition test is required. Automated introductory instructions appear and an input device is tested (Step 507) if a cognition test is required.

A system may determine if user input devices are operational and if an examinee demonstrates an understanding of these devices based on input signals received when an examinee operates them. A system may then determine if an examinee responds correctly (Step 508). An examinee who does not respond correctly will receive an output warning (Step 509) and repeat Step 507.

When an examinee responds correctly, cognition test administration (Step 510) initiates. Cognition test results are stored (Step 511). This data may be stored in a test result data component 125. When an examinee responds correctly (Step 512), an examinee may proceed to the next test (Step 516). An output warning (Step 513) is issued to an examinee who does not respond correctly to the queries (Step 512). Test completion is acknowledged (Step 514) and a program ends (Step 515).

Figure 6:
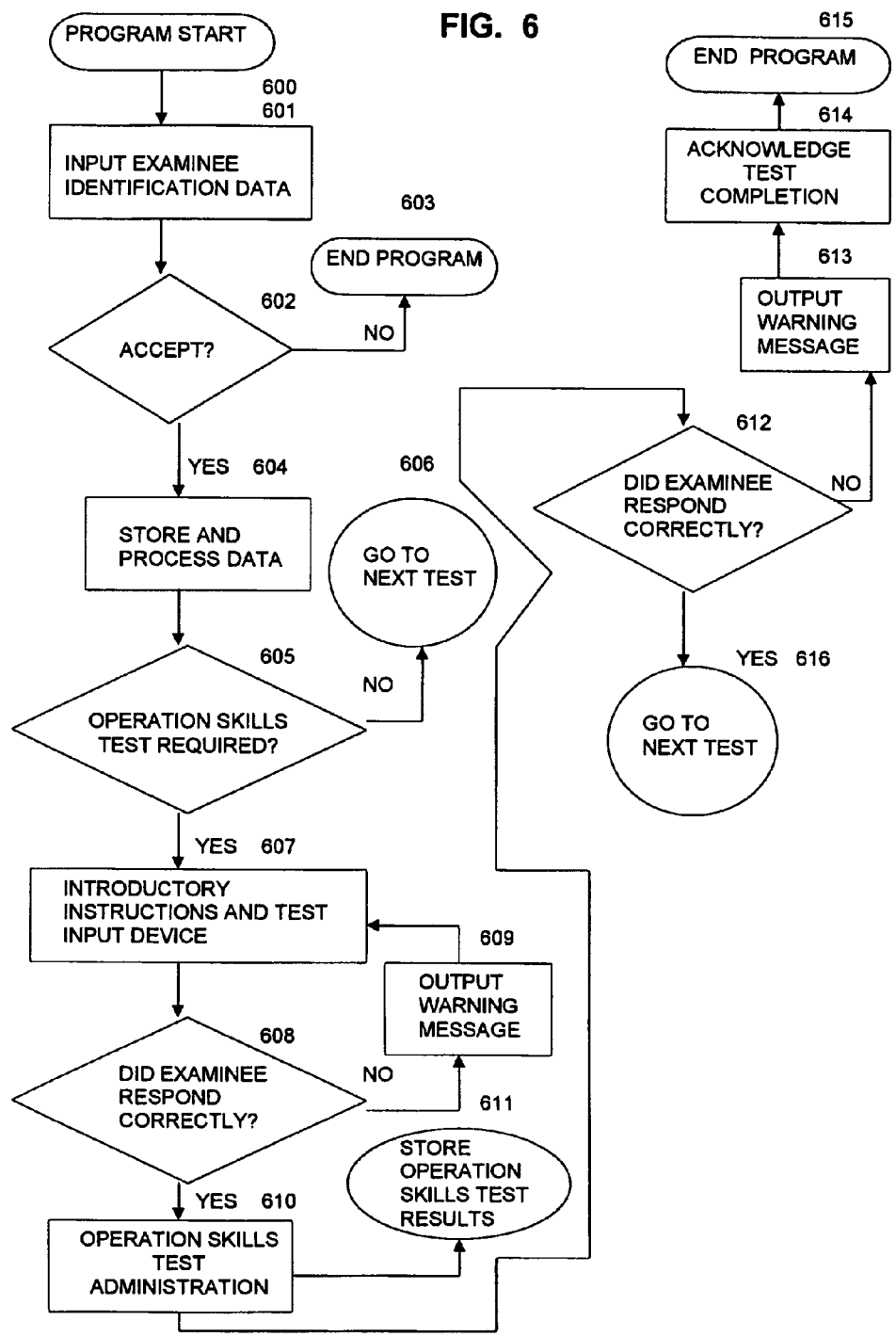
FIG. 6 shows an embodiment of a flowchart of an operation of steps for administering an operation skills test sequence.

FIG. 6 shows a flow chart for a specific operation of the steps for administering an operation skills test. In this process, a program starts (Step 600) with the prompting of an examinee for the input of identification data (Steps 601-602). A program ends (Step 603) if an examinee's identification data is rejected.

Once identification data is accepted, an examinee's data is stored and processed (Step 604). An examinee may proceed to the next test (Step 606) if an operation skills test (Step 605) is not required.

A system proceeds with prompting an examinee to respond (Step 605) to whether or not an operation skills test is required. Introductory instructions are provided and testing of an input device occurs (Step 607) if an operation skills test is required.

A system may then determine if an examinee responds correctly (Step 608). An examinee who does not respond correctly will receive an output warning (Step 609) and repeat Step 607.

When an examinee responds correctly, operation skills test administration (Step 6101 initiates. Operation skills test results are stored (Step 611). When an examinee responds correctly (Step 612), an examinee may proceed to the next test (Step 616). An output warning (Step 613) is issued to an examinee who does not respond correctly to the queries (Step 612). Test completion is acknowledged (Step 614) and a program ends (Step 615).

Figure 7:
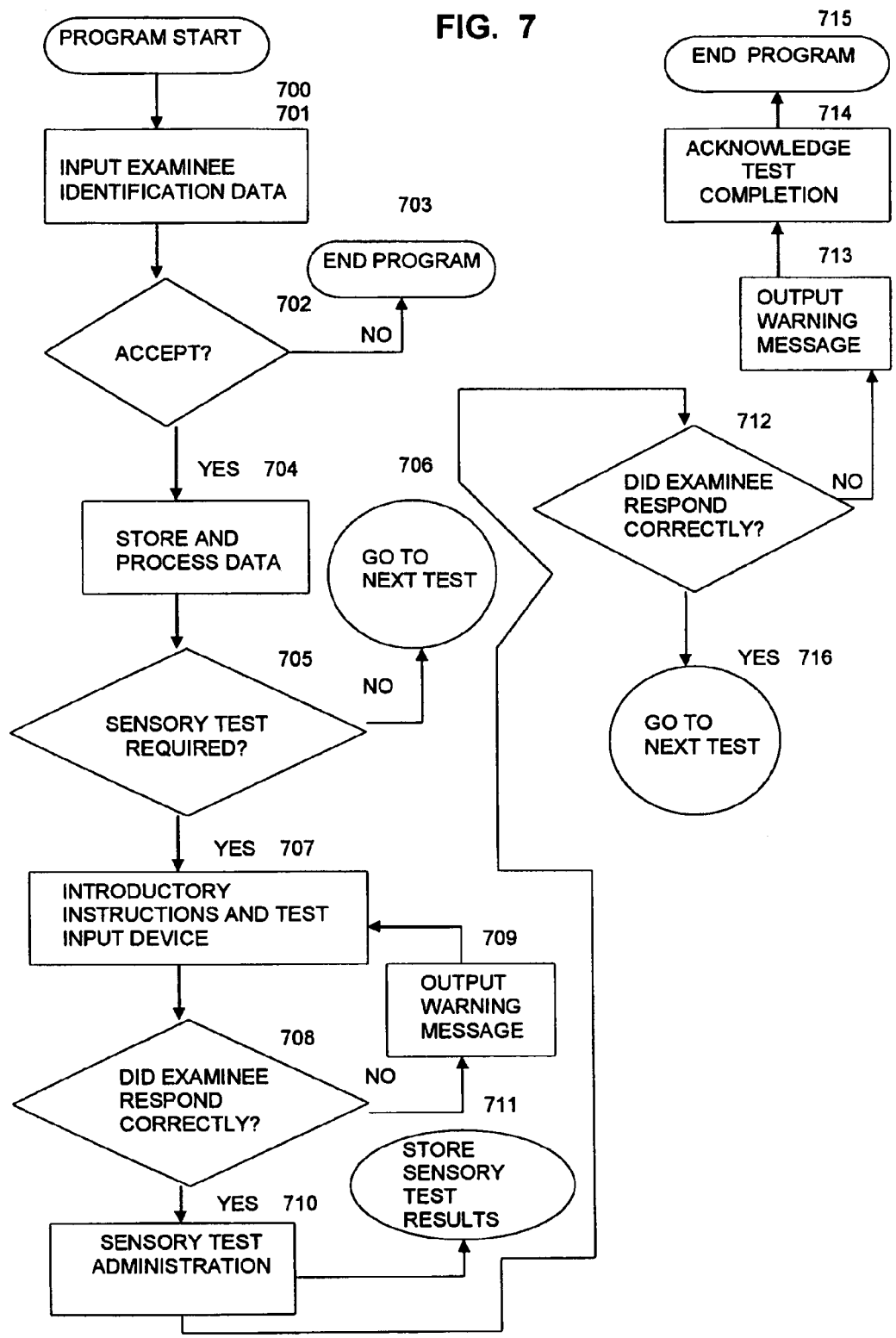
FIG. 7 shows an embodiment of a flowchart of an operation of steps for administering a sensation test sequence.

FIG. 7 shows a flow chart for the specific operation of the steps for administering a sensory test. In this process, a program starts (Step 700) with the prompting of an examinee for the input of identification data (Steps 701-702). A program ends (Step 703) if an examinee's identification data is not accepted. Once identification data is accepted, an examinee's data is stored and processed (Step 704). An examinee may proceed to the next test (Step 706) if a sensory test (Step 705) is not required.

A system proceeds with prompting an examinee to respond (Step 705) to whether or not a sensory test is required. Introductory instructions appear and testing of an input device occurs (Step 707). A system may then determine if an examinee responds correctly (Step 708). An examinee who does not respond correctly will receive an output warning (Step 709) and repeat Step 707.

When an examinee responds correctly, sensory test administration (Step 710) begins. Sensory test results are stored (Step 711). When an examinee responds correctly (Step 712), an examinee may proceed to the next test (Step 716). An output warning (Step 713) is issued to an examinee who does not respond correctly (Step 712). Test completion is acknowledged (Step 714) and a program ends (Step 715).

Figure 8:
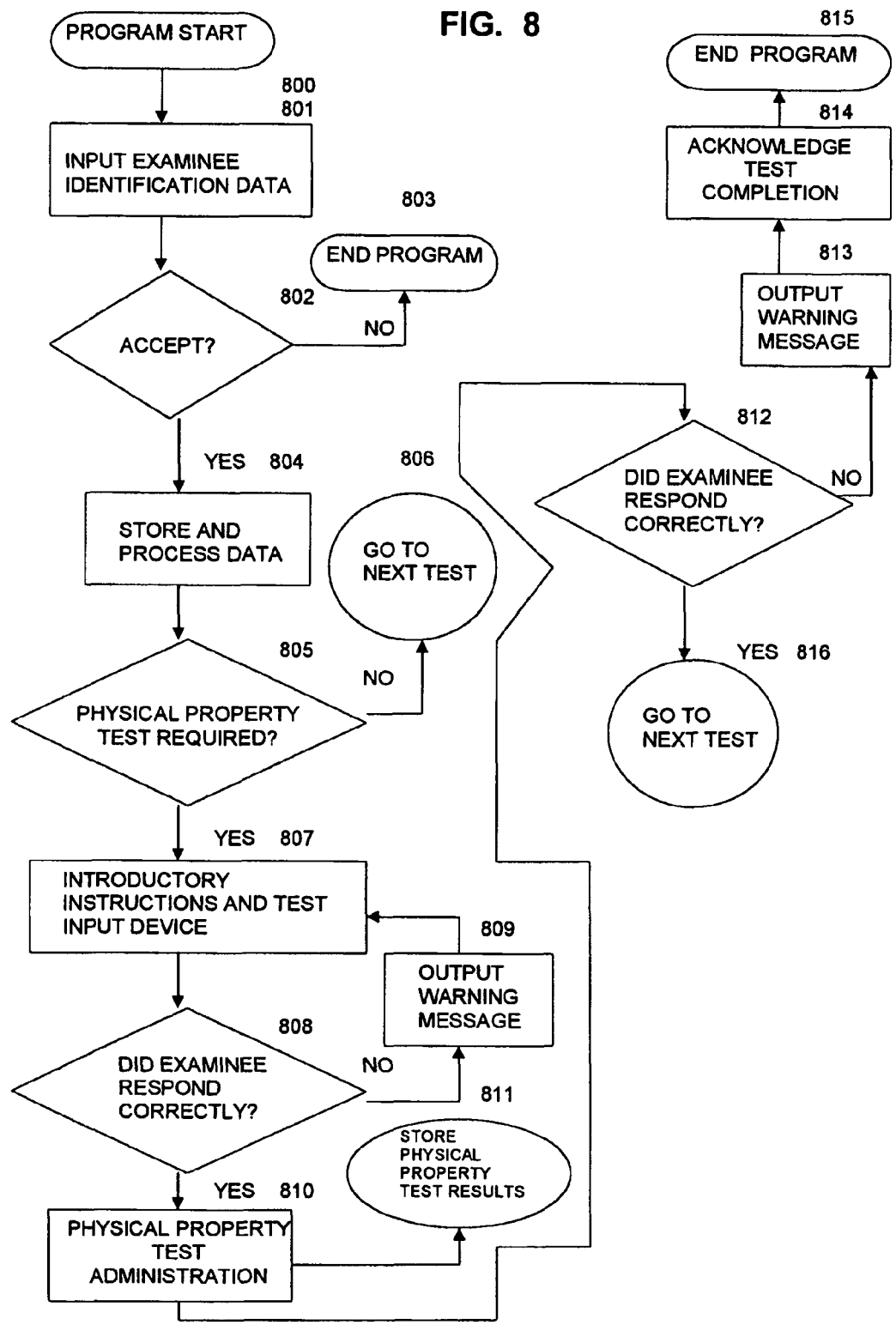
FIG. 8 shows an embodiment of a flowchart of an operation of steps for administering a physical property test sequence.

FIG. 8 shows a flow chart for the specific operation of the steps for administering a physical property test. In this process, a program starts (Step 800) with the prompting of an examinee for the input of identification data (Steps 801-802). A program ends (Step 803) if an examinee's identification data is not accepted.

Once identification data is accepted, an examinee's data is stored and processed (Step 804). An examinee may proceed to the next test (Step 806) if a physical property test (Step 805) is not required.

A system proceeds with prompting an examinee to respond (Step 805) to whether or not a physical property test is required. Introductory instructions appear and testing of an input device occurs (Step 807). A system may then determine if an examinee responds correctly (Step 808). An examinee who does not respond correctly will receive an output warning (Step 809) and repeat Step 807.

When an examinee responds correctly, physical property test administration (Step 810) begins. Physical property test results are stored (Step 811). When an examinee responds correctly (Step 812), an examinee may proceed to the next test (Step 816). An output warning (Step 813) is issued to an examinee who does not respond correctly to the queries (Step 812). Test completion is acknowledged (Step 814) and a program ends (Step 815).

Figure 9:
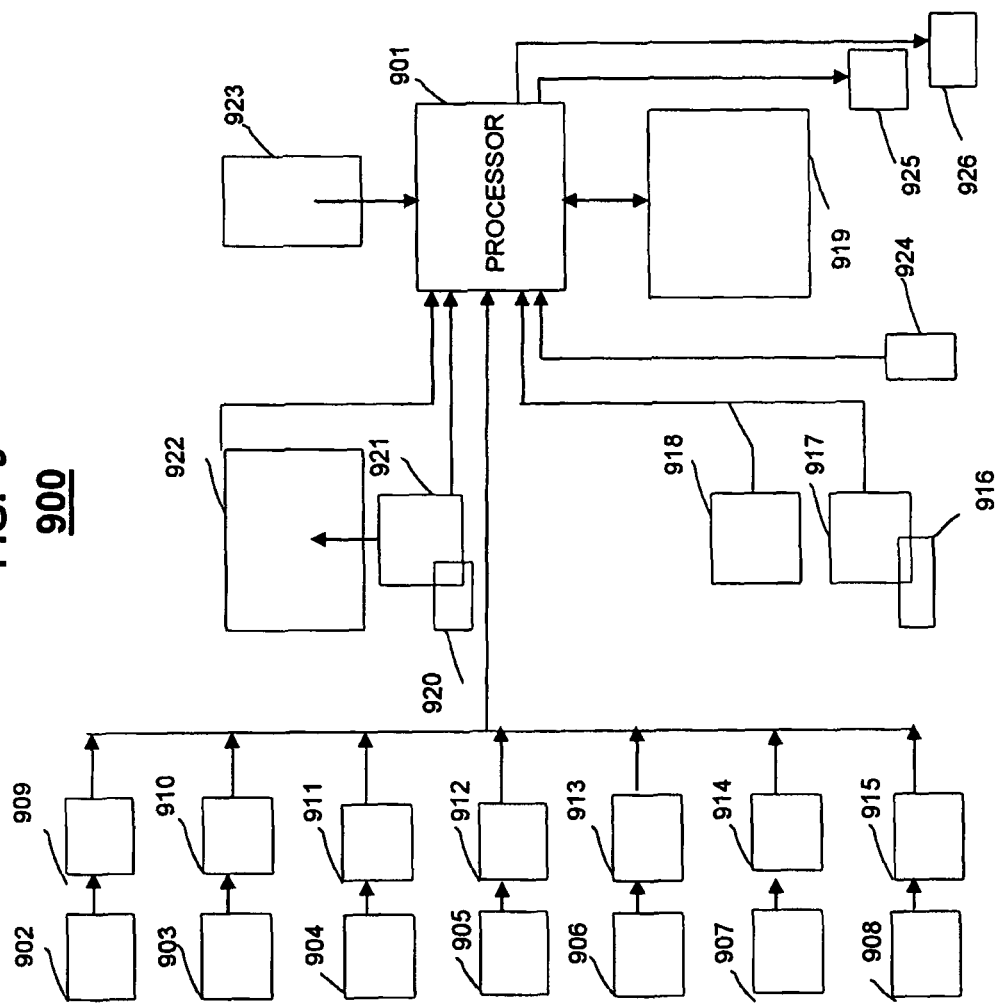
FIG. 9 shows an embodiment of a block schematic diagram of a control circuit for a sensory input device.

FIG. 9 shows an embodiment of a block schematic diagram of a control circuit for a Sensory Input Device. The Sensory Input Device includes a processor, for example a microprocessor, programmed to control at least one actuator interface within the Sensory Input Device. Several actuator interfaces include 909, 910, 911, 912, 913, 914, and 915 are shown for example only. Depending upon the functionality built into the Sensory Input Device there may be a number of such actuator interfaces or only a single one selected to effect actuation of a respective input function or functions. For example, Actuator Interface 909 is linked to an Auditory Input/Actuator 902 where sound may be inputted. Sound may be inputted to activate a program, a test, a sequence of tests, and/or respond to stimuli. In this example: Auditory Input/Actuator 902 is linked to Actuator Interface 909, Gustatory Input/Actuator 903 is linked to Actuator Interface 910. Kinesthetic Input/Actuator 904 is linked to Actuator Interface 911, Olfactory Input/Actuator 905 is linked to Actuator Interface 912. Tactile Input/Actuator 906 is linked to Actuator Interface 913. Vestibular Input/Actuator 907 is linked to Actuator Interface 914. Visual Input/Actuator 908 is linked to Actuator Interface 915.

Actuator Interface 909, as coupled to Auditory Input/Actuator 902, may allow for the inputting of sounds from a user whereby, for example, a sound of presence can be inputted. Such input could be combined with other input in a suitable environment. In another illustration, a loud speaker incorporated in a calculated dimensional object, or wearable to provide musical, voice or similar input which may be audible to the user or may provide an atmospheric change for example by being outside the human audible range provides, for example, low frequency contributions to the feel of the Sensory Input Device.

Actuator Interface 910, as coupled to Gustatory Input/Actuator 903, may allow for the inputting of tastes from a user whereby, for example, a taste of presence can be inputted. Such input could be combined with other input in a suitable environment Actuator Interface 911, as coupled to Kinesthetic Input/Actuator 904 may allow for the inputting of movement from a user whereby, for example, a movement, a motion, and/or a distinct action of presence can be inputted. Such input could be combined with other input in a suitable environment.

Actuator Interface 912, as coupled to Olfactory Input/Actuator 905, may allow for the inputting of scents from a user whereby, for example, a scent of presence can be inputted. Such input could be combined with other input in a suitable environment Actuator Interface 913, as coupled to Tactile Input/Actuator 906, may allow for the inputting of thermal/haptic properties, by touch, such as the input of cold, heat, pressure, and/or even pain from a user, whereby, for example, a touch of presence can be inputted, or even a change in temperature can be inputted or stimulated. Such input could be combined with other input in a suitable environment.

Actuator Interface 914, as coupled to Vestibular Input/Actuator 907, may allow for the inputting of balance from a user whereby, for example, a sense of presence can be inputted. Such input could be combined with other input in a suitable environment. Actuator Interface 915, as coupled to Visual Input/Actuator 908 may allow for the inputting of optical effects, color changes by electro optical effect, or simply visual input from a user. Such input could be combined with other input, such as the Kinesthetic Input/Actuator, in a suitable environment.

A location sensor 923 may be included. For example, a Global Positioning System (GPS) location sensor may be installed so that the response of the Sensory Input Device may be varied for different locations of the same Sensory Input Device. As an alternative to GPS, positioning devices such as Radio Frequency Identity Chips (RFID) could be used whereby activation of RFID modules are incorporated and placed at strategic points to identify a specific location of a Sensory Input Device.

The Sensory Input Device may include a display unit 926, for example, in the form of a Liquid Crystal Display (LCD) screen, to provide an output to the user or to assist with basic programming or setting up of the response required from the Sensory Input Device in respect of certain features of messages or conversations. The LCD may also be used to display the actual content of a received sensory message or even telepathic message. Output device 925 may provide printing functions, sensory output, or other programmable tasks as needed.

There may be several inputs to the processor 901 including, for example, a user interface 918 such as a touch screen, connectable keyboard, detector, pedal, steering wheel, or the like to enable inputs in respect of required responses for example. The user interface may be as simple as a detector which senses a squeeze of a single point to enable a yes/no type response in reply to an output although more complex arrangements could be employed if necessary.

As known by those in the art, user identification input device 924 improves security by identifying and/or verifying the identity of an examinee.

A program interface 917 is provided which may be designed to accept pre-programmed devices 916 such as a Read Only Memory (ROM) card which could reflect the modus operandi of the actuators 909-915 by modifying or developing the basic programming of a processor 901. To complete the functionality of a processor 901 there is a data store 919 or memory which contains the required parameters of operation of the processor 901. A Data Store may include but not be limited to software modules, test program, examinee identification data, and test result data storage, among others. Storage may be on or off site. As an example, there may be cloud storage whereby data is stored on multiple virtual servers that may be hosted by a third party.

The flexible inputs to the processor 901, those to which it is responsive to control the actuators 909 to 915 mainly comprise a communications receiver 922 which may be coupled to a message receiver such as a mobile phone, for example using the "Bluetooth" low power radio standard whereby a receiving device 921, for example a mobile phone, may be coupled to several items. Alternatively, the Sensory Input Device may incorporate a phone or Short Messaging Service (SMS) receiver 921 with its own programmable smart card 920, such as a Subscriber Identity Module (SIM) card whereby direct communication between a network and the Sensory Input Device may be achieved although such may limit the flexibility of the Sensory Input Device unless it also incorporates a communications receiver 922, such as an LPR receiver.

SMS technologies allow cellular network users to send a short ext message to other users.

A receiver 921 may either pass data directly to the processor 901 or may forward messages using LPR. In either event the response of the processor 901 is to analyze the content of the communication in order to derive actuations required, among others.

A connection device, such as a modem or other communication apparatus, may be incorporated to link to an interconnected network for data transmission, such as the Internet.

Figure 10:
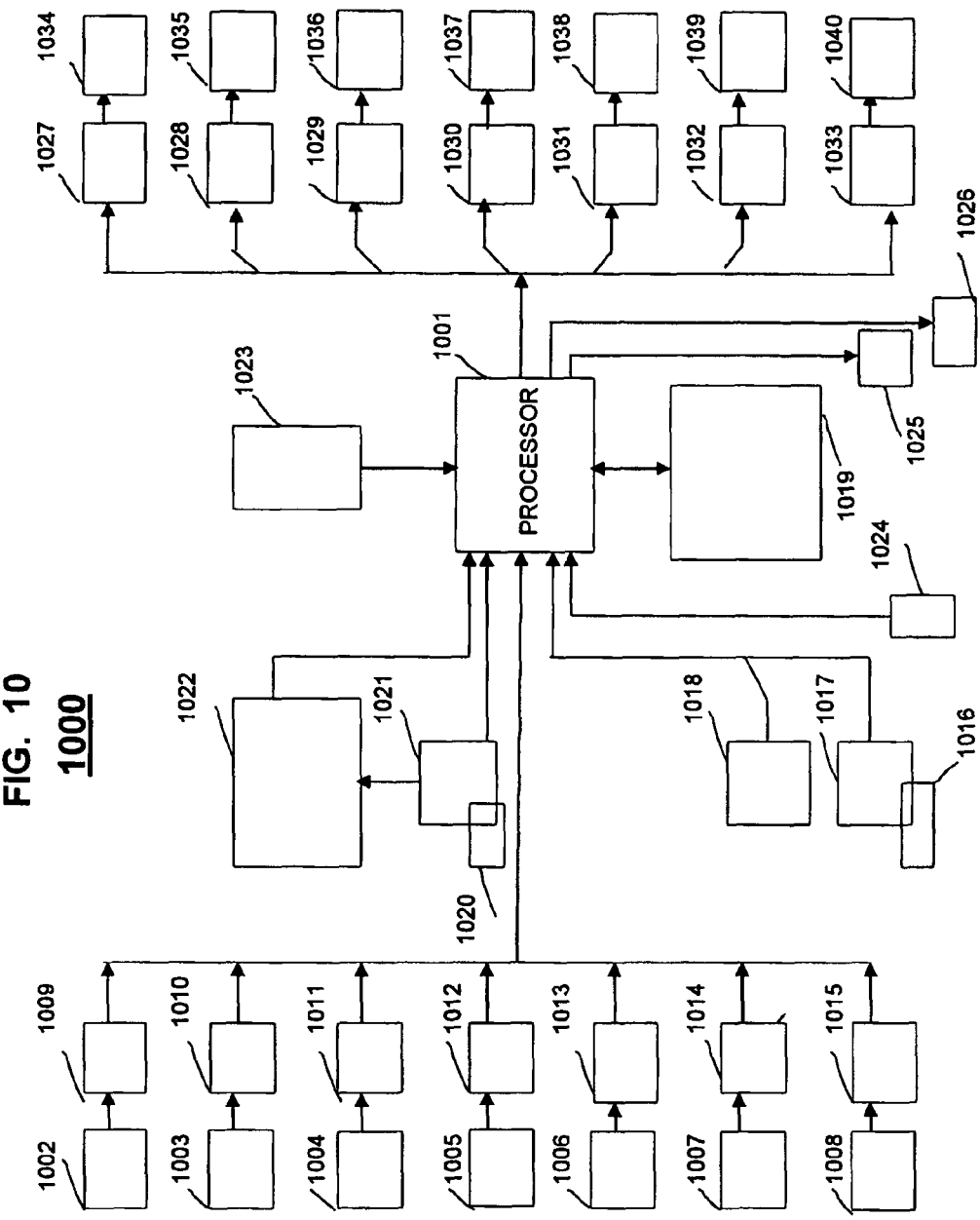
FIG. 10 shows an embodiment of a block schematic diagram of a control circuit for a sensory input and a sensory output device.

FIG. 10 shows an embodiment of a block schematic diagram of a control circuit for a sensory input device and a sensory output device. System 1000 includes a processor, for example a microprocessor, programmed to control at least one actuator interface within the sensory input device and sensory output device. Several actuator interfaces that couple with sensory input devices include 1009, 1010, 1011, 1012, 1013, 1014, and 1015 are shown for example only. Several actuator interfaces that pair with sensory output devices include 1027, 1028, 1029, 1030, 1031, 1032, and 1033 are shown for example only. Depending upon the functionality built into the sensory input device there may be a number of such actuator interfaces or only a single one selected to effect actuation of a respective input function or functions. There may also be a number of such actuator interfaces or only a single one selected to effect actuation of a respective output function or functions depending upon the functionality built into the sensory output device. For example. Actuator Interface 1009 is linked to an Auditory Input/Actuator 1002 where sound may be inputted. Sound may be inputted to activate a program, a test, a sequence of tests, and/or respond to stimuli.

In this example: Auditory Input/Actuator 1002 is linked to Actuator Interface 1009. Gustatory Input/Actuator 1003 is linked to Actuator Interface 1010. Kinesthetic Input/Actuator 1004 is linked to Actuator Interface 1011. Olfactory Input/Actuator 1005 is linked to Actuator Interface 1012. Tactile Input/Actuator 1006 is linked to Actuator Interface 1013. Vestibular Input/Actuator 1007 is linked to Actuator Interface 1014. Visual Input/Actuator 1008 is linked to Actuator Interface 1015.

Actuator Interface 1009, as coupled to Auditory Input/Actuator 1002, may allow for the inputting of sounds from a user whereby, for example, a sound of presence can be inputted. Such input could be combined with other input in a suitable environment. In another illustration, a loud speaker incorporated in a calculated dimensional object, or wearable to provide musical, voice or similar input which may be audible to the user or may provide an atmospheric change for example by being outside the human audible range provides, for example, low frequency contributions to the feel of the Sensory Input Device.

Actuator Interface 1010, as coupled to Gustatory Input/Actuator 1003, may allow for the inputting of tastes from a user whereby, for example, a taste of presence can be inputted. Such input could be combined with other input in a suitable environment. Actuator Interface 1011, as coupled to Kinesthetic Input/Actuator 1004 may allow for the inputting of movement from a user whereby, for example, a movement, a motion, and/or a distinct action of presence can be inputted. Such input could be combined with other input in a suitable environment.

Actuator Interface 1012, as coupled to Olfactory Input/Actuator 1005, may allow for the inputting of scents from a user whereby, for example, a scent of presence can be inputted. Such input could be combined with other input in a suitable environment. Actuator Interface 1013, as coupled to Tactile Input/Actuator 1006, may allow for the inputting of thermal/haptic properties, by touch, such as the input of cold, heat, pressure, and/or even pain from a user, whereby, for example, a touch of presence can be inputted, or even a change in temperature can be inputted or stimulated. Such input could be combined with other input in a suitable environment.

Actuator Interface 1014, as coupled to Vestibular Input/Actuator 1007, may allow for the inputting of balance from a user whereby, for example, a sense of presence can be inputted. Such input could be combined with other input in a suitable environment. Actuator Interface 1015, as coupled to Visual Input/Actuator 1008 may allow for the inputting of optical effects, color changes by electro optical effect, or simply visual input from a user. Such input could be combined with other input, such as the Kinesthetic Input/Actuator, in a suitable environment.

A location sensor 1023 may be included. For example, a Global Positioning System (GPS) location sensor may be installed so that the response of the Sensory Input Device may be varied for different locations of the same Sensory Input Device.

In this example: Auditory Output/Actuator 1034 is linked to Actuator Interface 1027. Gustatory Output/Actuator 1035 is linked to Actuator Interface 1028. Kinesthetic Output/Actuator 1036 is linked to Actuator Interface 1029. Olfactory Output/Actuator 1037 is linked to Actuator Interface 1030. Tactile Output/Actuator 1038 is linked to Actuator Interface 1031. Vestibular Output/Actuator 1039 is linked to Actuator Interface 1032. Visual Output/Actuator 1040 is linked to Actuator Interface 1033.

Actuator Interface 1027, as coupled to Auditory Output/Actuator 1034, may allow for the outputting of sounds from a user whereby, for example, a sound of presence can be outputted. Such output could be combined with other output in a suitable environment. In another illustration, a loud speaker incorporated in a calculated dimensional object, or wearable to provide musical, voice or similar output which may be audible to the user or may provide an atmospheric change for example by being outside the human audible range provides, for example, low frequency contributions to the feel of the Sensory Output Device.

Actuator Interface 1028, as coupled to Gustatory Output/Actuator 1035, may allow for the outputting of tastes from a user whereby, for example, a taste of presence can be outputted. Such output could be combined with other output in a suitable environment.

Actuator Interface 1029, as coupled to Kinesthetic Output/Actuator 1036 may allow for the outputting of movement from a user whereby, for example, a movement, a motion, and/or a distinct action of presence can be outputted. Such output could be combined with other output in a suitable environment.

Actuator Interface 1030, as coupled to Olfactory Input/Actuator 1037, may allow for the outputting of scents from a user whereby, for example, a scent of presence can be outputted. Such output could be combined with other output in a suitable environment.

Actuator Interface 1031, as coupled to Tactile Output/Actuator 1038, may allow for the outputting of thermal/haptic properties, by touch, such as the output of cold, heat, pressure, and/or even pain from a user, whereby, for example, a touch of presence can be outputted, or even a change in temperature can be outputted or stimulated. Such output could be combined with other output in a suitable environment.

Actuator Interface 1032, as coupled to Vestibular Output/Actuator 1039, may allow for the outputting of balance from a user whereby, for example, a sense of presence can be outputted. Such output could be combined with other output in a suitable environment.

Actuator Interface 1033, as coupled to Visual Input/Actuator 1040 may allow for the outputting of optical effects, color changes by electro optical effect, or simply visual output from a user. Such output, such as the Kinesthetic Output/Actuator, could be combined with other output in a suitable environment.

As an alternative to GPS, positioning devices such as Radio Frequency Identity Chips (RFID) could be used whereby activation of RFID modules are incorporated and placed at strategic points to identify a specific location of a Sensory Output Device. The Sensory Input Device and Sensory Output Device may include a display unit 1026, for example, in the form of a Liquid Crystal Display (LCD) screen, to provide an output to the user or to assist with basic programming or setting up of the response required from the Sensory Input Device and Sensory Output Device in respect of certain features of messages or conversations. The LCD may also be used to display the actual content of a received sensory message or even telepathic message. Output device 1025 may provide printing functions, sensory output, and/or other programmable tasks as needed.

There may be several outputs to a processor 1001 including, for example, a user interface 1018 such as a touch screen, connectable keyboard, detector, pedal, steering wheel, or the like to enable inputs in respect of required responses for example. The user interface may be as simple as a detector which senses a squeeze of a single point to enable a yes/no type response in reply to an output although more complex arrangements could be employed if necessary.

As known by those in the art, user identification input device 1024 improves security by identifying and/or verifying the identity of an examinee.

A program interface 1017 is provided which may be designed to accept pre-programmed devices 1016 such as a Read Only Memory (ROM) card which could reflect the modus operandi of the actuators 1009-1015 and/or actuators 1027 to 1033 by modifying or developing the basic programming of a processor 1001. To complete the functionality of a processor 1001 there is a data store 1019 or memory which contains the required parameters of operation of the processor 1001. A Data Store may include but not be limited to software modules, test program, examinee identification data, and test result data storage, among others.

The flexible inputs to a processor 1001, those to which it is responsive to control the actuators 1009 to 1015 mainly comprise a communications receiver 1022 which may be coupled to a message receiver such as a mobile phone, for example using the "Bluetooth" low power radio standard whereby a receiving device 1021, for example a mobile phone, may be coupled to several items. Alternatively, the Sensory Input Device may incorporate a phone or Short Messaging Service (SMS) receiver 1021 with its own programmable smart card 1020, such as a Subscriber Identity Module (SIM) card whereby direct communication between a network and the Sensory Input Device may be achieved although such may limit the flexibility of the Sensory Input Device unless it also incorporates a communications receiver 1022, such as an LPR receiver. SMS technologies allow cellular network users to send a short ext message to other users.

A receiver 1021 may either pass data directly to the processor 1001 or may forward messages using LPR. In either event the response of the processor 1001 is to analyze the content of the communication in order to derive actuations required, among others. Alternatively, a connection device, such as a modem or other communication apparatus, may be incorporated to link to an interconnected network for data transmission, such as the Internet.

Figure 11:
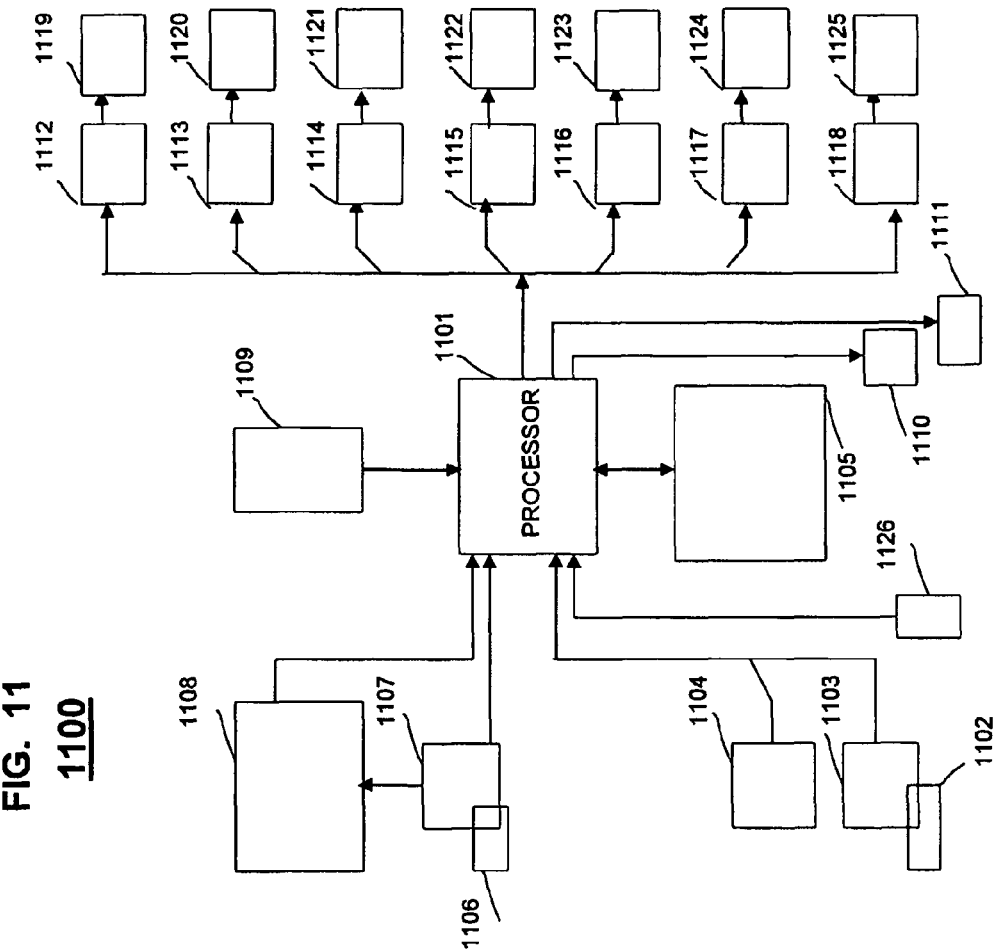
FIG. 11 shows an embodiment of a block schematic diagram of a control circuit for a sensory output device.

FIG. 11 shows an embodiment of a block schematic diagram of a control circuit for a sensory output device.

System 1100 includes a processor, for example a microprocessor, programmed to control at least one actuator interface within the sensory output device. Several actuator interfaces that couple with sensory output devices include 1112, 1113, 1114, 1115, 1116, 1117, and 1118 are shown for example only. Depending upon the functionality built into the sensory output device there may be a number of such actuator interfaces or only a single one selected to effect actuation of a respective output function or functions. There may also be a number of such actuator interfaces or only a single one selected to effect actuation of a respective output function or functions depending upon the functionality built into the sensory output device.

For example, Actuator Interface 1112 is linked to an Auditory Output/Actuator 1119 where sound may be outputted. Sound may be outputted to activate a program, a test, a sequence of tests, and/or respond to stimuli.

A location sensor 1109 may be included. For example, a Global Positioning System (GPS) location sensor may be installed so that the response of the Sensory Output Device may be varied for different locations of the same Sensory Output Device.

In this example: Auditory Output/Actuator 1119 is linked to Actuator Interface 1112. Gustatory Output/Actuator 1120 is linked to Actuator Interface 1613. Kinesthetic Output/Actuator 1121 is linked to Actuator Interface 1114. Olfactory Output/Actuator 1122 is linked to Actuator Interface 1115. Tactile Output/Actuator 1123 is linked to Actuator Interface 1116. Vestibular Output/Actuator 1124 is linked to Actuator Interface 1117. Visual Output/Actuator 1125 is linked to Actuator Interface 1118.

Actuator Interface 1112, as coupled to Auditory Output/Actuator 1119, may allow for the outputting of sounds from a user whereby, for example, a sound of presence can be outputted. Such output could be combined with other output in a suitable environment. In another illustration, a loud speaker incorporated in a calculated dimensional object, or wearable to provide musical, voice or similar output which may be audible to the user or may provide an atmospheric change for example by being outside the human audible range provides, for example, low frequency contributions to the feel of the Sensory Output Device.

Actuator Interface 1113, as coupled to Gustatory Output/Actuator 1120, may allow for the outputting of tastes from a user whereby, for example, a taste of presence can be outputted. Such output could be combined with other output in a suitable environment.

Actuator Interface 1114, as coupled to Kinesthetic Output/Actuator 1121 may allow for the outputting of movement from a user whereby, for example, a movement, a motion, and/or a distinct action of presence can be outputted. Such output could be combined with other output in a suitable environment.

Actuator Interface 1115, as coupled to Olfactory Input/Actuator 1122, may allow for the outputting of scents from a user whereby, for example, a scent of presence can be outputted. Such output could be combined with other output in a suitable environment.

Actuator Interface 1116, as coupled to Tactile Output/Actuator 1123, may allow for the outputting of thermal/haptic properties, by touch, such as the output of cold, heat, pressure, and/or even pain from a user, whereby, for example, a touch of presence can be outputted, or even a change in temperature can be outputted or stimulated. Such output could be combined with other output in a suitable environment.

Actuator Interface 1117, as coupled to Vestibular Output/Actuator 1124, may allow for the outputting of balance from a user whereby, for example, a sense of presence can be outputted. Such output could be combined with other output in a suitable environment.

Actuator Interface 1118, as coupled to Visual Input/Actuator 1125 may allow for the outputting of optical effects, color changes by electro optical effect, or simply visual output from a user. Such output, such as the Kinesthetic Output/Actuator, could be combined with other output in a suitable environment.

As an alternative to GPS, positioning devices such as Radio Frequency Identity Chips (RFID) could be used whereby activation of RFID modules are incorporated and placed at strategic points to identify a specific location of a Sensory Output Device.

A Sensory Output Device may include a display unit 1111, for example, in the form of a Liquid Crystal Display (LCD) screen, to provide an output to the user or to assist with basic programming or setting up of the response required from the Sensory Input Device and Sensory Output Device in respect of certain features of messages or conversations. The LCD may also be used to display the actual content of a received sensory message or even telepathic message. Output device 1110 may provide printing functions, sensory output, or other programmable tasks as needed.

There may be several inputs to a processor 1101 including, for example, a user interface 1104 such as a touch screen, connectable keyboard, detector, pedal, steering wheel, or the like to enable inputs in respect of required responses for example. The user interface may be as simple as a detector which senses a squeeze of a single point to enable a yes/no type response in reply to an output although more complex arrangements could be employed if necessary.

As known by those in the art, user identification input device 1126 improves security by identifying and/or verifying the identity of an examinee.

A program interface 1103 is provided which may be designed to accept pre-programmed devices 1102 such as a Read Only Memory (ROM) card which could reflect the modus operandi of the actuators 1112-1118 by modifying or developing the basic programming of a processor 1101. To complete the functionality of a processor 1101 there is a data store 1105 or memory which contains the required parameters of operation of the processor 1101. A Data Store may include but not be limited to software modules, test program, examinee identification data, and test result data storage, among others.

The flexible inputs to the processor 1101, those to which it is responsive to control the actuators 1112 to 1118 mainly comprise a communications receiver 1108 which may be coupled to a message receiver such as a mobile phone, for example using the "Bluetooth" low power radio standard whereby a receiving device 1107, for example a mobile phone, may be coupled to several items.

Alternatively, the Sensory Output Device may incorporate a phone or Short Messaging Service (SMS) receiver 1107 with its own programmable smart card 1106, such as a Subscriber Identity Module (SIM) card whereby direct communication between a network and the Sensory Output Device may be achieved although such may limit the flexibility of the Sensory Output Device unless it also incorporates a communications receiver 1108, such as an LPR receiver.

SMS technologies allow cellular network users to send a short ext message to other users. A receiver 1107 may either pass data directly to a processor 1101 or may forward messages using LPR. In either event the response of a processor 1101 is to analyze the content of the communication in order to derive actuations required, among others.

Operation

According to one aspect of a preferred embodiment, an apparatus of the system generally incorporates means for displaying at least one of vision, cognition, knowledge, sensation, physical properties, or related images to an examinee; means for generating such image data, such as a means for transportation for a vehicle in motion (such as a road, space, track, or water) for simulating operation of a vehicle in motion to be outputted on a display means; means for generating instruction data to be outputted at least on the display means; means for sensing; means for sensory inputting; means for activating; means for processing, and storing personal information data; means for using personal information data for restablishing identification or authentication; means for inputting response data from the examinee in response to the generated image data on the display means; means for activating; means for sensory outputting; and means for controlling operation of the display means, the image data generating means, the instruction data generating means, and the inputting means.

Controlling means includes components for screening at least one of vision, cognition, operation skills, physical properties, sensation, or the like.

In another embodiment, screening components are operatively connected to image data generating means, instruction data generating means, and inputting means such that image data and instruction data are generated and displayed in coordination with the screening test sequences conducted by the said screening components, respectively, and response data inputted through inputting means.

Controlling means may also include components for controlling a mechanism or a system as an actuator controls such mechanism(s) and/or system(s).

Alternative Embodiments

Of course it will be recognized that a wide range of changes and modifications, apparent to those skilled in the art, can be made to the preferred embodiments described above.

The following describes some alternative embodiments:

A system, apparatus, and method for automatic tests and/or communications are conducted over a computing device, network, thin client, or any interconnected means for data exchange and storage, such as Internet(s), Intranet(s), or extranet(s), independent of location. A component for identification and authentication purposes may be incorporated to authenticate, establish, update, or modify the identity of the examinee.

To conduct such examinations, stimuli of different shape, size, speed, frequency, location, color, dimensionality, modality, sensation, contrast, and/or intensity are displayed on the user's display model. Use of such stimuli affords, for example, a convenient manner for conducting computerized mechanisms of screening, testing, training, educating, and/or communicating.

The test results may be automatically outputted in raw form (i.e., pure data, numbers), in sensory output, or processed by the system before being outputted. As one of skill in the art would understand, test results may be processed, rated, correlated, iced, stored, shared, or any combination thereof.

Any device that accepts information in digital or similar form and manipulates it for a result based on a sequence of instructions, such as a computer, mainframe, minicomputer, workstation or personal computer, network computer, plurality of network computers, or the like could be used with any embodiments described above. In addition, any forms that execute automation, applications, or operating systems could benefit from the presently preferred embodiments.

Computerized device(s) can be powered through various mechanisms. One example would include a disposable or rechargeable battery unit. Another example of a power source would include a plug for connecting the device directly into a wall outlet. Another example would include a solar source for power.

Alternative embodiments may include but not be limited to the use of desktop(s), laptop(s), palmtop(s), or thin client computer(s), among other computing devices.

In some embodiments, a system may consist of a computer network with a file server connected to a plurality of terminals as opposed to stand-alone computers. Each terminal would include a display, the input/interface devices and a local CPU circuit that received, transmitted or processed data with the central file server in running the test sequences.

Tests may be combined. One of skill in the art would understand that the order and duration of test sequences may be switched. Further, operation of a system may include the use of one or more test sequences illustrated, wherein different combinations and orders of test sequences are implemented. Even more, each separate test sequence may even consist of a combination of individual tests, such as a vision function test, a vision status test, and a vision condition test. Each separate test sequence may also consist of varying numbers of individual tests. The order and number of test sequences and individual tests would depend on the requirements of the particular application, as would be understood by one of skill in the art.

Still further, input responses and output responses to tests may automatically integrate sensation and/or sensory stimuli—whether or not sensation is actually measured as component of a test For example, a vision test may incorporate sensory stimuli such as olfactory stimuli to optimize testing whereas a sensation test may also integrate optical, color, or other visual sensory stimuli.

These and other changes and modifications are to be understood as included within the scope of the improved automatic systems and methods, as defined by the appended claims, unless they depart the refrom.

Another embodiment is directed to a method for establishing fixation during automatic measurement and evaluation of at least one of vision, cognition, operation skills, physical property, sensation, or the like, particularly useful when conducted over a data transmission and exchange system, for example, as embodied in the system of FIG. 1A. It should be clearly understood, that the presently preferred embodiments is also applicable for use with other systems and methods that automatically assess at least one of a subject's vision, cognition, operation skills, physical property, sensation, or related capabilities.

Another embodiment is directed to a method for presenting false-positive and false-negative test stimuli to the subject, to ensure reliability, the details of such techniques being well known to those skilled in the art.

One of skill in the art knows that the preferred embodiments described above include an option for automatic feedback and results since client requirements may dictate whether or not such data and/or information are issued to examinee(s). Therefore, autonomous testing methods, scoring, immediate output (such as feedback), and even sensory output may be available to the examinee.

Another embodiment is directed to automatically authenticating the identity of a subject prior to and immediately after automatic administration of at least one of each test, test query, test question, test screen, display, or any combination thereof. The details of such techniques are well known to those skilled in the art.

In another embodiment, all functions of the apparatus are in each case controlled by way of at least one of the pertaining form that executes automation, such as software, an online program, or other data control mechanism and can be varied with respect to the type of the construction possibilities and/or configuration mechanisms.

In still another alternative embodiment, the system may comprise software, as well as a combination of software and hardware. It additionally may comprise an interconnected system of one or more workstations, electronic computing devices, and or automatic means of transmitting data.

In another embodiment, the system may comprise adaptable computer programs accessible to the computers and or work stations via either CDs, DVDs, external drives, flash drives, interne, intranet, or any other method for transporting and/or exchanging information.

Another embodiment may also provide customized individual packages, as well as multiple workstations connected to a network or a website.

Another embodiment may also comprise a database that may store responses and/or historical data of each user. The database may be local, wireless, and/or remote, and may be accessible via a data transmission and exchange system, such as the Internet or may be fully or partially available at a user's facilities. The remote storage and, or database may therefore constitute cloud storage and/or management.

Still another embodiment adjusts to educating a user with respect to measured performance level or need for safety tool. The educating tasks may involve gaming and/or sensing elements to further enhance the motivation of the user. The tasks preferably may start with easy problems and gradually may increase in the level of challenge. The use of immediate feedback, as well as elements of competition when appropriate, may be included.

Still further, another embodiment provides at least one of brain fitness, eye fitness, brain training, eye training, sensory exercises, and other visual and/or cognitive exercises to teach and/or improve vision, sensation, senses, and/or cognition, among others.

While the embodiments described above may be customized to the optimal challenge level for the user, based on past and current performance analysis with online dynamic diagnosis of errors and biases, there are a variety of ways to screen the same basic skills and produce the relevant scientific information.

In another embodiment, alternative forced-choice procedure measures, in which examinees must discriminate which of the test stimuli differs from the others, are integrated through the design permitting this discrimination and hence defines the level of screening. Such stimuli may include but not be limited to Snellen ratio, optotype size, optotype speed, optotype color, optotype dimensionality, optotype position, optotype contrast, and/or sensory stimuli. Measures may include but not be limited to static visual acuity, dynamic visual acuity, sensory stimuli quantification, or the like. Dynamic Visual Acuity defines the ability of an observer to discern details of an object while either the observer and/or the object is in motion.

In a further embodiment, computerized images may contain letters, numbers, characters, sceneries, sensations, sensory stimuli, and/or sounds and may be arranged in row(s), size(s), strings, movement, or any combination thereof and include at least one letter, character, sensation, or object in a different orientation, color, pattern, sensation, or any combination thereof than the others presented on the image and to be read and responded to by an examinee.

The embodiments described above may include high versus low contrast stimuli used to screen visual acuity at smaller and larger characters, according to calculated measures, such as Snellen ratios, where the position of the dissimilar character varies randomly across repeated test trials on a di splay screen.

In another embodiment, multilingual capabilities and assistive technology features, specifically those designed to actively engage examinees with disabilities, may include but are not limited to such features as automatic instruction, audio, text, tests, feedback, or the like. Such features may or may not incorporate sensation, sensory stimuli, and/or physical property parameters. Sensory stimuli may be especially beneficial for those who physically and/or mentally lack the ability to engage in traditional tests and automated test settings.

Still further, another embodiment may also consist of methods of automatically determining the presence and amount of substances, such as toxins, carcinogens, alcohol, inhalants, pharmaceuticals, or illegal narcotics. Such substances may impact at least one of vision, cognition, operation skills, physical property, or sensation of subjects.

Embodiments described above may also be used to provide primary and/or supplementary screening of those who operate vehicles in motion.

Embodiments described above may include a feature and/or components that promotes security and uniquely identifies subjects through mechanisms such as at least one of auditory recognition, biological recognition, biometric recognition, bodily circulation recognition, bodily fluid recognition, bodily motion recognition, bodily odor recognition, bodily part recognition, bodily sound recognition, bodily temperature recognition, bodily touch recognition, brain pattern recognition, chemical recognition, dental recognition, eye recognition, facial recognition, fingerprint recognition, genetic marker recognition, gustatory recognition, handwriting recognition, hologram recognition, iris recognition, lingual recognition, mnemonic recognition, neuroimaging recognition, olfactory recognition, pattern of finger lengths recognition, personal data, personal recognition, personal signature recognition, physical property recognition, position recognition, retina recognition, space recognition, telemetric recognition, thought recognition, time recognition, vestibular recognition, visual recognition, voiceprint recognition, or any combination thereof.

In another embodiment, image data generating means automatically incorporates transportation image data, such as a road, and test pattern image data. The test pattern image data is structured to screen at least one of vision, cognition, operation skills, physical property, sensation or any combination thereof such as those required for a vehicle in motion.

In a further embodiment, a transportation license application is provided through methods for measuring and evaluating at least one of vision, cognition, operation skills, physical property, sensation, and/or related conditions and capabilities. These may incorporate the steps of providing a display through which transportation image data and instruction data are presented to an examinee, conducting a calculated test sequence with the examinee, and providing input devices through which the subject may respond to the said test sequences. Such input devices may comprise sensory input devices to optimize measurement and evaluation of examinees. A calculated test sequence includes at least one of conducting a vision test sequence with the examinee, conducting a cognition test sequence with the examinee, or conducting an operation skills test sequence with the examinee. The steps for conducting a test sequence each includes at least one of the steps of simulating the operation of a vehicle in motion to be presented on the display, generating instruction data for providing instructions for the examinee during the screening test sequences, or determining whether the inputted response data is correct or incorrect.

Another embodiment provides an automatic method for comprehensively screening at least one of vision, cognition, operation skills, physical property, sensation, or related capabilities of the masses.

In another embodiment, automatic systems and methods allow for automatic mass measurement and evaluation of at least one of vision, cognition, operation skills, physical property, sensation, or the like.

Another embodiment includes a processor that determines from the analyzed data the stimuli appropriate for at least one of the visual, cognitive, operation skills, physical property, sensation, or related level.

In still another embodiment, a representation generator, for at least one of vision, cognition, physical property, sensation, or related skills, operably coupled to a tester generates an overall representation using an examinee's responses. This representation may be used in a variety of diagnostic processes.

Another embodiment provides a computer software storage device that includes a program that executes the described method. The automatic method may be used for screening at least one of dementia, Alzheimer's disease, Parkinson disease, or any other neuropsychological, movement, and/or neuromotor conditions.

There is yet additionally provided another embodiment that teaches an automatic method for diagnosing cognitive ability of an examinee, including the steps of screening a cognitive level of an examinee and comparing the screened cognitive level to data stored in a database, so as to at least one of measure, diagnose, monitor, or evaluate conditions such as dementia, Alzheimer's disease, Parkinson disease, Traumatic Brain Injury, learning disabilities, cognitive injury, and/or other cognitive disorder or disease.

In another embodiment, instant feedback on strengths and weaknesses maneuvering adverse conditions are provided to an examinee. When operating a vehicle in motion, such as a motor vehicle, adverse conditions include but are not limited to at least one of the following: transportation site features(such as pavement), slippery pavement, various weather conditions (such as snow, rain, wind, dust, fog, smoke, haze) solar glare, night glare, ambient lighting conditions, traffic volumes, pedestrian movements, or vehicle mechanical problems (such as a blown tire). Vehicle mechanical problems may be involuntary (such as a failed engine or motor) or voluntary (such as control (such as a steering wheel, pedal, etc.) and/or misuse), among others. The automation, integration, sensation, and/or simulation of such conditions and situations are obvious to those skilled in the art.

Still further is another embodiment that teaches an automatic method for at least one of educating, screening, or testing examinees and others on adverse conditions. The method(s) may include the steps of presenting stimuli relevant to adverse conditions, receiving motion input from the examinee in response to a stimulus, analyzing the aspects of at least one of cognitive, visual, operation skills, physical property, sensation, or related capabilities of the input, interpolating the analyzed aspects as these relate to vehicles in motion, adjusting a stimulus according to the analyzed aspect, and repeating the steps of presenting, receiving, analyzing, interpolating and adjusting one or more times.

In another embodiment, additional software and/or networking may be included with the device to allow for the automatic screening of at least one of vision, cognition, operation skills, physical property, sensation, related conditions, capabilities, or the like. For example, a test for school age children, may involve more game-like apparatuses, systems, and methods. Such mechanisms may involve the use of camera-like screening instruments, as an example.

Another embodiment teaches cognition measurement and evaluation following a stroke, a head injury, or other type of trauma-related cognitive decline, as well as alcohol or drug related decline.

In another embodiment, a distributed system is created using a tester Web server operably coupled to a browser via the Internet. The tester Web server serves pages to the browser implementing this system.

In another embodiment, a measurement apparatus includes an electronic test pattern for display of test patterns to an examinee, an examinee response input device for recording an examinee's response to a test pattern, and a tester operably coupled to both for conducting the measurement.

Another embodiment includes a database for storing the analyzed data, where the data may relate to at least one of the norms, probabilities, or statistics of at least one of vision, cognition, operation skills, physical property, sensation, or the like. Analyzed data may be data regarding motor skills, complex/continuous motor skills, time required to move the stimulus, movement smoothness, complex eye hand coordination, hand-hand coordination, and/or eye-foot coordination.

Another embodiment includes a database for automatically storing and analyzing identification authentication data to readily identify an examinee. The system may also include a video and/or audio input and/or output device to automatically provide instructions in one or several different languages.

In another aspect of the presently preferred embodiment, a selected visual field test pattern is presented to a subject with an automatic means to prevent cheating and dishonorable test-taking practices, such as randomization of visual field test patterns. The user may select a missing or distorted visual field test pattern using an input device, when a random series of visual field test patterns, such as those of differing contrasts, are presented to the user. The user's responses are automatically recorded and evaluated. Automatic output is provided as at least one of feedback, results, scores, reviews, classifications, rejections, simplified output, pass/fail determinations, graphical/statistical representations, or comparative analyses. Such input, feedback, and/or output may be sensory.

In another embodiment, vision, cognition, physical property, sensation, and related representations are automatically correlated with known causes of vision, physical property, sensation, and/or cognition defects. These are stored in a diagnostic database operably coupled to a diagnostic tool configured to perform multiple functions, such as a server, accessible via a connectivity device that facilitates data transmission, such as the Internet, a local network, or some wireless network A representation is automatically sent to the diagnostic tool which uses an artificial intelligence engine to establish a diagnosis.

Another embodiment teaches an automatic method for diagnosing at least one of cognitive, visual, physical property, sensory, or related ability of a user, including the steps of testing at least one of cognitive, visual, physical property, sensation, or related level of a user and comparing at least one of cognitive, visual, physical property, sensation, or related level to, for example, data stored in a database, so as to diagnose at least one of brain diseases, brain injuries, brain disorders, eye diseases, eye injuries, eye disorders, physical property disorders, sensory disorders, and/or various neuro-motor disorders. These include but are not limited to age-related macular degeneration, autism, Alzheimer's disease, dementia, diabetic retinopathy, glaucoma, Parkinson disease, heart disease, sensory dysfunction, and learning disabilities, among others.

In another embodiment, test presentations may be automatically adjusted to eliminate inattention or reduce the incidence of aftereffects that can develop, especially when, for example, simulators, such as driving simulators, are incorporated in the evaluation process.

Another embodiment provides the icing of storage and the collation of data through at least one of a locally, remotely, wirelessly, or virtually centralized database. This allows the automatic tracking of vision, cognition, operation skills, physical property, sensation, and related measurement and evaluation programs.

In still another alternative embodiment, customized reporting may be provided for studies, such as epidemiological studies, and can be tailored to virtually any specific request.

In an alternative embodiment, a vehicle in motion is reliably simulated so that an examinee feels as if he or she is actually operating a vehicle in motion.

In yet another embodiment, at least one of a driving simulator, display device, or the like is used so that an examinee does not tire easily, is swiftly and adequately screened, has easy access to all of the controls, and experiences little or no adverse reactions such as cyber sickness, driving simulator sickness, or the like.

An alternative embodiment automatically simulates a vehicle in motion.

In another embodiment, a mechanism that simulates an environment of a vehicle in motion may also produce immediate physical property, visual, sensory, or audio response to an examinee's manipulation of such an apparatus.

In still another alternative embodiment, at least one of a display device, a simulator (such as a driving simulator), or the like may be optionally used as an educational tool to demonstrate how to respond to adverse conditions.

In one possible embodiment, a low-cost driving simulator or other device that simulates environments and situations to train, test, and/or educate examinees may be used to measure and evaluate at least one of vision, cognition, operation skills, physical property, sensation, or the like. Such simulation may offer the benefit of self-customization, among other features, to reduce the likelihood of simulator sickness, which results from a disparity between the actual visual image position verses the expected position in a dynamic situation. Hence the testing should be done as effectively and as swiftly as possible, without compromising thoroughness. This will reduce the incidences of simulator sickness and aftereffects.

Some embodiments may also allow for the objective and rapid evaluation of individuals with strokes, cognitive maladies, and other neurological disorders, such as Parkinson's disease, a progressive, neurodegenerative disease characterized by tremor and impaired muscular coordination. Traditional testing methods of dementia patients tend to be time-consuming and challenging.

In a further embodiment, there are automatic assessments such as strength, general mobility, head flexibility, neck flexibility, working memory, visualization of missing data, visual attention, field of view, and/or visual search, etc. among others, of examinees.

In another embodiment, a simulator is used to screen at least one of vision, cognition, operation skills, physical property, or sensation responses to ambient lighting, or adverse conditions for educational purposes, clinical reviews, medical evaluations, military reviews, licensure to operate a vehicle in motion, or any combination thereof.

In an alternative embodiment, at least one of an examinee's visual capabilities, cognitive capabilities, operation skills, physical property measures, sensation abilities, or the like are measured and evaluated by automatically exposing the examinee to certain conditions, such as ambient light conditions.

In another embodiment, conditions such as glaucoma, diabetic retinopathy, cataracts, and Age-related Macular Degeneration, low vision, autism, stroke, head injury, dementia, depression, Alzheimer's disease, Parkinson disease, Post Traumatic Stress Disorder, and other possible neuromotor, neuropsychological, neurological, and medical conditions, among others, may be automatically detected and monitored. Some conditions, such as Traumatic Brain Injury, may not be evident until days, weeks, months, or even years after an impact event. Therefore, automatic testing offers many benefits over traditional evaluations.

Embodiments of automatic systems, methods, and apparatuses may also aid in detection and treatment of sensation problems where one or more senses lack and/or are affected in individuals.

In an alternative embodiment, an examinee's knowledge is assessed through responses to a display of select matter as it relates to a specific mode of transport, such as street signs, traffic control devices, pavement markings, signal devices, railroad signs, air flight control signs, space travel signs, and maritime signs, among others.

In a further embodiment, sensory stimuli are used to screen vision, such as visual acuity, according to calculated measures, such as Snellen ratios, where the position of the dissimilar character varies randomly across repeated test trials on a display screen.

In another embodiment, at least one of authentication identification data of examinees and test fraud prevention mechanisms improve safety and security.

Another embodiment directs the automatic detection of at least one of attention disorders, learning disabilities, Alzheimer's disease, dementia, diabetic retinopathy, Attention Deficit Hyperactivity Disorder (ADHD), stroke/ischemia, Traumatic Brain Injury, mental retardation, Post Traumatic Stress Disorder (PTSD), cataracts, visual impairment, heart disease, and other similar disorders.

Another embodiment directs the use of sensory input, such as at least one of auditory input, gustatory input, kinesthetic input, olfactory input, tactile input, vestibular input, visual input, or any combination thereof for the inputting of data to enhance at least one of measurement, evaluation, security, safety, training, and/or communications.

Still another embodiment directs the use of sensory output, such as at least one of auditory output, gustatory output, kinesthetic output, olfactory output, tactile output, vestibular output, visual output, or any combination thereof for the outputting of data to enhance at least one of measurement, evaluation, security, safety, training, and or communications.

Still another embodiment directs sensory input and sensory output, at least one selected from auditory input, gustatory input, kinesthetic input, olfactory input, tactile input, vestibular input, visual input, or any combination thereof and at least one selected from auditory output, gustatory output, kinesthetic output, olfactory output, tactile output, vestibular output, visual output, or any combination thereof for inputting and outputting of data to enhance at least one of measurement, evaluation, security, safety, training, and/or communications.

In another embodiment, automatic measurement, evaluation, security, safety, training, and/or communications actively engage those with movement disorders, neurological disease, and disorders such as Amyotrophic Lateral Sclerosis (ALS), chronic pain, dystonia, epilepsy, essential tremor, Muscular Dystrophy, MD, Huntington's Disease, Multiple Sclerosis (MS), Muscular Dystrophy, and Parkinson's disease.

In another embodiment, automatic responses, such as instant scores, feedback, and/or self-corrections are provided as sensory output.

In another embodiment, a clock is displayed whereby any one of seven senses described herein are used to provide sensory input to illustrate at least one of a clock, the digits on a clock, a clock face, or the like. Examples include but are not limited to drag and drop mechanisms, number writing, or other forms of automated illustration in calculated dimensionality and/or modality.

In another embodiment, an automated trail making test is presented where by automatic responses are provided through sensory output. For example, a correct and/or incorrect connection may yield at least one of sound, taste, movement, scent, touch, balance, color, temperature, or any combination thereof to indicate whether or not a correct trail is connected. Sensory input, to enhance the testing experience, may also be provided and processed. Still further, an actual instrument may be projected in a calculated dimension and/or appear as a hologram.

In one embodiment, a Clock Drawing Test is used to automatically measure and evaluate cognition through response to at least one of a blank image, a pre-drawn circle, or a pre-drawn clock through at least one of sensory input, sensory output, or any combination thereof as described herein. Still further, the actual instrument may be projected in a calculated dimension.

In another embodiment, a Clock Drawing Test is used to automatically measure and evaluate cognition through displaying at least one of a plurality of positions of clock hands, clock faces, numbers, letters, symbols.

In another embodiment, a Clock Drawing Test is used to automatically measure and evaluate cognition through displaying stimuli that represent a calculated shape of a clock face, calculated position of clock hands, a plurality of clock face shapes, a plurality of clock face numbers, and a plurality of numbers in a calculated sequence on a clock face.

In another embodiment, sensory devices described herein enhance communications, such as telecommunications, and enable those who may have physical in abilities to effectively communicate through at least one of seven different senses.

Still further, another embodiment incorporates sensory devices described herein to improve automated voting techniques and systems.

Advantages

In view of the disadvantages and shortcomings present in the prior art, improved automatic systems and methods provide valuable measurements and evaluations of at least one of vision, cognition, operation skills, physical property, sensation, or the like.

The preferred embodiments described above provide important advantages. In clinical testing, these embodiments provide particularly effective testing of a subject, allowing objective and economical measures. In transportation applications, these embodiments offer rapid testing and monitoring of the masses who obtain or maintain a license to operate a vehicle in motion. In military settings, these embodiments afford uniform screening tools for recruits, soldiers, and veterans. In security, education, and health, these embodiments offer standardization and equality. Importantly, automatic systems and methods promote safety on and of the transportation infrastructure.

The advantages achieved by the embodiments described above are that a small and handy measuring apparatus was created in contrast to the known large systems. The combination of the possible measuring operations permits the concentration of the functions of several systems on a single apparatus, which measures the important vision, cognition, operation skills, physical property, sensation, and related functions. Such evaluations and measurements are cost-effective and eco-friendly because they provide rapid, objective, and, importantly, automatic testing for the purposes and benefits of at least one of medicine, law enforcement, military, safety, security, or transportation, among others.

As a result of the construction with low-cost elements and the utilization of existing elements (computer), it is possible to integrate the system into already existing systems. This results in a significant reduction of costs and a savings of space, energy, and potential e-waste, especially when unitary housing is integrated for all tests. Because the apparatus can be used without any problems in normal daylight, the operation becomes uncomplicated and convenient. Summarizing, there is the possibility for wide-spread use of the methods, apparatuses, and systems for example, also among hospitals, security agencies, militaries, schools, industries, organizations, prisons, and transport license bureaus, among others. As screening tests, these low-cost apparatuses may contribute to the detection, diagnosis, and, ultimately, treatment of dangerous conditions, diseases, disorders, and/or injuries. Within this scope, algorithms of any forms that execute automation already provide information with respect to measured values.

Still another major advantage of the presently preferred embodiment over the prior art is that the automatic technique may be employed for the masses of individuals who might not be easily tested using the prior art methods that employ non-automated devices. Hence these embodiments are beneficial in applications where trained ophthalmologists, physicians, and other clinicians are not available, such as driver's license test bureaus, rural areas, prisons, outer space (such as NASA or any agency or entity associated with space travel) applications, maritime environments, flight settings, security facilities, or military applications.

The presently preferred embodiment offers exceptional advantages when measuring and evaluating examinees at or away from transportation license agencies, such as a driver's license test bureaus, particularly if the identification authentication component is utilized for identification purposes of the examinee.

Other examples of the utility of the presently preferred embodiment include the automatic screening of individuals suffering from at least one of brain injury, brain trauma, brain disease, cognitive deficit, eye disease, eye injury, eye trauma, neuropsychological disorders, or movement disorders (such as neuromotor disorders), heart disease, physical property injury, physical property disease, and/or sensation dysfunction. Such individuals may often not be aware that that they have such a condition, malady, or disorder through the use, if any, of other traditional testing devices and/or methods.

In view of the disadvantages and shortcomings present in the prior art, automatic measurements improve systems, methods, and apparatuses to provide valuable evaluations and assessments of at least one of vision, cognition, operation skills, physical property, sensation, or the like.

From the description above, a number of advantages of some embodiments of our automatic systems, methods, and apparatuses become evident:

(a) An improved system, method, and apparatus is presented for optimizing automatic evaluation and measurement using sensation and physical properties.

(b) Automatic evaluation and measurement of an examinee's brain is achieved using techniques such as neuroimaging.

(c) An automatic assessment of mental abilities using non-verbal methods, verbal methods, non-invasive methods, or any combination thereof is accomplished.

(d) Interactive assessments simplify the processes of stimuli response.

(e) Output is displayed in calculated dimensions, such as one, two, three, or more dimensions.

(f) Responses are inputted in one, two, three, or more dimensions.

(g) A diagnostic quality of image or other data is automatically achieved.

(h) Physical measures, such as head-neckflexibility, leg strength, arm strength, hand strength, phalange strength, and general mobility, among others, are automatically quantified.

(i) Innovative medical imaging techniques optimize evaluations and measurements of the masses.

(j) Test fraud prevention measures are improved through enhanced security and automated security measures.

(k) Identification of subjects is further improved through a larger menu of identification methods than presently available.

(l) Safety and security are effectively improved as larger segments of the population are ultimately identified, measured, and evaluated.

(m) A superior tool is available for efficient and accurate data collection, analysis and distribution by integration of the latest technological advances.

(n) An automatic administration of tests is designed to minimize cultural bias.

(o) Automatic instructions are directly or indirectly provided to subjects.

(p) Automatic collection of data reduces costs associated with labor and equipment.

(q) Sensory input facilitates the input process for those who lack the ability to use traditional and widely used input devices.

(r) New tests, test updates, and updates of data analysis software are easily integrated.

(s) Data may be remotely accessible via local or remote (such as cloud) computing techniques.

(t) These objects and others are achieved by integrating sensory input device(s) and/or sensory output device(s).

(u) Staff costs are effectively reduced.

(v) Wait time is effectively reduced.

(w) There are benefits associated with early detection, early intervention, and/or early treatment (to prevent or limit the advancing of a specific disease and/or condition).

(x) Paper and pencil tests are effectively eliminated.

(y) There is a reduction, if not elimination, of human administration, review, and/or scoring of tests.

(z) A testing process is standardized.

(aa) Equal access to testing of speakers of other languages and those with physical inabilities and limitations is provided.

(bb) Variability in test administration is effectively eliminated.

(cc) Potential sources of error and bias are effectively eliminated.

(dd) A means to test large populations is accomplished.

(ee) Eco-friendly methods are provided since tress are not destroyed for paper and wood products.

(ff) The disabled are effectively empowered and engaged in the testing and/or communication processes.
(gg) Communication is improved between users.
(hh) Safety in at least one of transportation infrastructure, schools, prisons, militaries, hospitals, industries, or organizations is accomplished by enhanced automation of testing and/or communications.
(ii) E-wastes are effectively reduced since apparatuses, methods, and systems described herein can be easily upgraded and integrated.
(jj) Testing, training, screening, evaluating, and/or communicating easily integrates sensation for response to stimuli.
(kk) Embodiments provide vision, voice, sound, and/or movement to those who may lack it.
(ll) Methods and compositions described herein also provide treatment and/or enhancement of a cognitive state.
(mm) An improved system, method, and apparatus for automatic evaluation and measurement are presented.
(nn) Senses are stimulated to optimize evaluation and measurement of the mosses beyond that presently achievable by known systems, apparatuses, or methods.
(oo) An embodiment that automatically empowers the disabled without a requirement for human intervention is provided.
(pp) An embodiment that integrate speakers of other languages in the testing process without a requirement for manual (human) translation is achieved.
(qq) An embodiment that improves of testing whether or not it is related to a specific disease state, injury, and/or disorder is presented.
(rr) An embodiment that improves communication between users is accomplished.
(ss) Aspects of a system are capable of incorporating quantitative and qualitative measures of subjects through mechanisms of sensory input and/or sensory output, among others.
(tt) Automatic methods, apparatuses, and systems presented herein are needed and will greatly improve the clinical treatment for diminished cognitive ability (whether related to a specific neurodegenerative disease, hypoxia, stroke or similar disorder) and/or diminished visual ability (whether related to a specific injury, disease, or condition), among others.
(uu) Those with sensory integration dysfunction, those who experience difficulty maintaining balance and performing tasks that require coordinated use of opposing muscle groups (such as wringing out a cloth), among others may especially benefit from enhanced systems, methods, and apparatuses described herein.
(vv) Uniquely, physical property input may be inputted and sensory output outputted. Similarly, sensory input may be inputted and physical property outputted. These enhance testing and communications unlike any presently available.
(ww) Automatic voting machines may also benefit from sensory input and/or output techniques to reduce tampering and restore trust in voting processes.

CONCLUSION, RAMIFICATION, SCOPE

Thus it is obvious that at least one embodiment of a sensory input device, sensory output device, and automatic systems, methods, and apparatuses provide a more reliable yet economical structure that is accessible to almost any age group.
Although descriptions of specific embodiments are provided, many additional modifications and variations would be apparent to those skilled in the art. It is therefore to be understood that such embodiments may be practiced otherwise than as specifically described. Thus, the present embodiments should be considered in all respects as illustrative and not restrictive, the scope to be determined by claims supported by this application and the equivalents thereof.

Many additional modifications and variations may be made in the techniques and structures described and illustrated herein without departing from the spirit and scope herein.

All of these capabilities are developing to enhance a subject's testing experience and limit the impact on the environment.

Sensory input devices and sensory output devices are therefore effectively used to measure and evaluate at least one of cognition, knowledge, operation skills, physical properties, sensation, vision, or the like.

Sensory input devices and sensory output devices are also integrated to enhance communications.

Such applications, among others, may include a plurality of sensors, actuator interfaces, or any combination thereof to optimize performance.

The importance of automatic testing spans the areas of communication, education, health, industry, law, medicine, military, politics, private sector, safety, security, space, and transportation, among others.

What is claimed is:

1. An automatic system for testing, evaluating, screening, training, or any combination thereof for at least one of vision, cognition, knowledge, operation skills, physical properties, or sensation of a subject comprising: a computer for processing data wherein a computing environment is conducted over a network, thin client, or interconnected means for data exchange and storage; an input device for recording response information from a subject in response to test stimuli; a mechanism to offer an option for feedback a linking device for linking data to at least one institution whereby said data can be automatically stored, shared, reviewed, referred, and/or studied; a display device configured for presenting test stimuli to a subject and for displaying the test data received by the input device; wherein said computer means includes: a means for preventing test fraud; a means for identifying the subject; a user identification input device, a sensory input device, an actuator, a sensory output device, and a processing device for receiving said data from said input device to at least evaluate, identify, screen, test, train, or any combination thereof a personal condition of said subject.

2. An automatic system as claimed in claim 1, wherein the means for identifying a subject includes at least one of auditory recognition, biological recognition, biometric recognition, bodily circulation recognition, bodily fluid recognition, bodily motion recognition, bodily odor recognition, bodily part recognition, bodily sound recognition, bodily temperature recognition, bodily touch recognition, brain pattern recognition, chemical recognition, dental recognition, eye recognition, facial recognition, fingerprint recognition, genetic marker recognition, gustatory recognition, handwriting recognition, iris recognition, lingual recognition, mnemonic recognition, neuroimaging recognition, olfactory recognition, pattern of finger lengths recognition, personal data, personal recognition, personal signature recognition, physical property recognition, position recognition, radio frequency (RFID tags), retina recognition, space recognition, telemetric recognition, thermal pattern recognition, thought recognition, time recognition, vestibular recognition, visual recognition, voiceprint recognition, or any combination thereof.

3. An automatic system as claimed in claim 1 that automatically performs at least one of a display, response, data storage, data transmission, interpretation of data, or any combination thereof in the form of at least one of a hologram, computer-generated hologram, medical imaging, brain imaging, neuroimaging, X-ray imaging, Magnetic resonance imaging (MRI), nuclear magnetic resonance imaging (NMRI), electrical impulse imaging, visual imaging, or any combination thereof.

4. An automatic system as claimed in claim 1, wherein the input device is selected from at least one of an accelerator pedal, brake pedal, camera, computer mouse, hologram, horn, joystick, keyboard, physical measure device, microphone, physical property device, sensor, sensory device, sensory input device, steering wheel, telepathic input device, touch screen, video device, virtual reality device, wireless mouse and pad, X-ray, control device fitted with motion sensors, interactive screen, any other device capable of detecting an individual's response to testing stimuli, or any combination thereof.

5. An automatic system as claimed in claim 1, wherein the user identification input device includes at least one of biometrics, information data, password, radio frequency (RFID tags), thermal imaging, sensation metrics, sensory measures, or any combination thereof.

6. An automatic system as claimed in claim 1, wherein the display device is selected from at least one of a chemical simulation, dimensional display, driving simulator, electronic display, hologram, monitor, neural simulation, physical property display, printer, sensor, sensory device, sensory output device, simulator, telepathic output device, virtual reality, or any combination thereof.

7. An automatic system as claimed in claim 1, wherein the computer means is selected from at least one of a desktop, a laptop, a mainframe, a minicomputer, a network computer, a palmtop, personal computer, a processor, a telecommunication device, a thin client computer, a workstation computer, or plurality of computers.

8. An automatic system as claimed in claim 1, wherein the personal condition includes at least one of an age-related macular degeneration (AMD), Alzheimer's disease, Attention Deficit Disorder, autism, brain disease, brain injury, brain trauma, dementia, eye disease, eye injury, eye trauma, diabetic retinopathy, glaucoma, heart disease, hyperactivity, learning disabilities, neurological conditions, neuromotor conditions, neuropsychological conditions, Parkinson disease, physical disability, physical property diseases, physical property injuries, Post Traumatic Stress Disorder, sensory conditions, stroke, Traumatic Brain Injury, or any combination thereof.

9. An automatic system as claimed in claim 1, wherein the institution is selected from at least one of clinics, colleges, government agencies, hospitals, industries, law enforcement agencies, militaries, non-government organizations, prisons, private entities, schools, senior citizen centers, space stations, transportation bureaus, or any combination thereof.

10. An automatic system as claimed in claim 1, wherein the test stimuli differ in at least one of color, composition, concept, contrast, dimensionality, distribution, elements, frequency, geometric transformation, intensity, location, modality, movement, sensation, shape, size, sound, spatiality, speed, taste, temperature, texture, thought, time, touch, or velocity.

11. An automatic system as claimed in claim 1, wherein said test stimuli comprise at least one of a correct time sequence, proper numerology of clocks, trail making test, clock drawing test, visual attention sequence, executive function sequence, visual processing sequence, verbal memory test, nonverbal memory test, calculated symbols (such as letters, numbers, geometric shapes, colors, objects, dimensional symbols, among others), spatiality, calculated measurements, calculated depth, calculated sensation, calculated shapes, calculated sequence, calculated modality, physical property characterization, calculated dimensionality, alternating alphanumeric sequence, numeric sequence, contrast sensitivity, visual field, sound, sensation, visual acuity, dynamic visual acuity, static visual acuity, vision, working memory, verbal fluency, transportation routes, transportation exercises, actual clock, permutated clock, proper representation of time, hands representing time (such as years, weeks, months, hours, minutes, seconds), digital representation of a clock, dial representation of a clock, proper anatomy of a clock, visuospatial skills, executive function, random sequence, sequence based on stimuli, sensation, physical properties, physical property characterization, sensory simulation, physical properties, calculated trail, calculated metrics, calculated measurements, permutated clock, actual clock, clock face shape, or any combination thereof.

12. An automatic system as claimed in claim 1, wherein the means for preventing test fraud includes at least one of biometrics, data protection, false tests, randomization of screens, automatic observations of screens, automatic observations of displays, frequent authentication, passwords, secure computing mechanisms (such as Secure Socket Layers, cameras, videos), electronic monitoring, or sensory metrics.

13. A method for automatically testing, evaluating, screening, training, or any combination thereof for at least one of cognition, knowledge, operation skills, physical property, sensation, or vision of a subject comprising the steps of:
  (a) providing an identity means which is able to authenticate, establish, identify, validate, verify, or any combination thereof the identity of a subject,
  (b) providing an instruction means which is able to directly or indirectly communicate to said subject,
  (c) providing a display means through which stimuli, such as sensory stimuli, are presented,
  (d) conducting a test sequence with said subject based on said stimuli,
  (e) providing an input means, such as a sensory input means, through which said subject may respond to said stimuli, wherein said steps of conducting a test sequence each includes the steps of generating test data for simulating a test to be presented on said display, generating instruction data prior to test sequence administration, processing an inputting of response data during said test sequences, generating further instruction data based on determining whether said inputted response data is correct or incorrect,
  (f) providing an activating means through which a sensory device is coupled to an actuator interface,
  (g) providing a computing means to compute data which is inputted,
  (h) providing a processing means through which data is analyzed, compiled, correlated, interpreted, scored, shared, or any combination thereof,
  (i) providing a memory means through which said data is securely collected and stored,
  (j) providing an output means, such as a sensory output means, through which said data is outputted,
  (k) providing a detecting means through which at least one of conditions, deficits, diseases, or injuries of said subject may be identified, and
  (l) providing a security means through which data, identity of subject, or any combination thereof is protected.

14. The method of claim 13 further comprising the step of automatically identifying a subject by at least one of auditory recognition, biological recognition, biometric recognition, bodily circulation recognition, bodily fluid recognition, bodily motion recognition, bodily odor recognition, bodily part recognition, bodily sound recognition, bodily temperature recognition, bodily touch recognition, brain pattern recognition, chemical recognition, dental recognition, eye recognition, facial recognition, fingerprint recognition, genetic marker recognition, gustatory recognition, handwriting recognition, iris recognition, lingual recognition, mnemonic recognition, neuroimaging recognition, olfactory recognition, pattern of finger lengths recognition, personal data, personal recognition, personal signature recognition, physical property recognition, position recognition, radio frequency (RFID tags), retina recognition, space recognition, telemetric recognition, thermal pattern recognition, thought recognition, time recognition, vestibular recognition, visual recognition, voiceprint recognition, or any combination thereof.

15. The method of claim 13 further comprising the step of selecting sensory stimuli from at least one of auditory stimuli, gustatory stimuli, kinesthetic stimuli, olfactory stimuli, tactile stimuli, vestibular stimuli, visual stimuli, or any combination thereof.

16. The method of claim 13 further comprising the step of automatically responding to the inputting of a response, such as at least one of instant scores, self-corrections, corrections, feedback, cognitive feedback, sensory feedback, or physical property feedback.

17. The method of claim 13 further comprising the step of varying at least one of one of color, composition, concept, contrast, dimensionality, distribution, elements, frequency, intensity, location, modality, movement, sensation, shape, size, sound, spatiality, speed, taste, temperature, texture, thought, time, touch, or velocity of such test stimuli.

18. The method of claim 13 further comprising the step of automatically computing at least one of physical, cognitive, conceptual, sensory, virtual, visual, or physical property measures.

19. The method of claim 13 further comprising the step of automatically providing a security means by at least one of data protection, display observations, frequent authentication, passwords, secure computing mechanisms (such as Secure Socket Layers), cameras, videos, electronic monitoring, sensory metrics, false tests, randomization of screens, automatic observations of screens, automatic biometrics, physical property recognition, pre-verification method, credentialed, or at a calculated time interval, such as at least one of the start of testing, the time of response(s) to test stimuli, the end of testing.

* * * * *